United States Patent
Shelton, IV et al.

(10) Patent No.: US 9,814,514 B2
(45) Date of Patent: Nov. 14, 2017

(54) ELECTROSURGICAL (RF) MEDICAL INSTRUMENTS FOR CUTTING AND COAGULATING TISSUE

(71) Applicant: Ethicon Endo-Surgery, Inc., Cincinnati, OH (US)

(72) Inventors: Frederick E. Shelton, IV, Hillsboro, OH (US); David C. Yates, West Chester, OH (US); Chester O. Baxter, III, Loveland, OH (US); John V. Hunt, Cincinnati, OH (US); Jennifer M. Mallow, Cincinnati, OH (US); Barry C. Worrell, Centerville, OH (US); Taylor W. Aronhalt, Loveland, OH (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 88 days.

(21) Appl. No.: 14/026,662

(22) Filed: Sep. 13, 2013

(65) Prior Publication Data

US 2015/0080891 A1     Mar. 19, 2015

(51) Int. Cl.
*A61B 18/12* (2006.01)
*A61B 18/14* (2006.01)
(Continued)

(52) U.S. Cl.
CPC .......... *A61B 18/12* (2013.01); *A61B 18/1447* (2013.01); *A61B 18/1482* (2013.01);
(Continued)

(58) Field of Classification Search
CPC . A61B 18/12; A61B 18/1442; A61B 18/1445; A61B 18/1447; A61B 18/1482;
(Continued)

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| DE | 29623113 U1 | 10/1997 |
| DE | 20004812 U1 | 9/2000 |

(Continued)

OTHER PUBLICATIONS

International Search Report for PCT/US2014/052505, dated Mar. 30, 2015 (6 pages).

(Continued)

*Primary Examiner* — Daniel Fowler

(57) ABSTRACT

An electrosurgical device is disclosed. The electrosurgical device includes a handle, a shaft extending distally from the handle, and an end effector coupled to a distal end of the shaft. The end effector comprises a first electrode and a second electrode. The second electrode includes a first position and a second position. The second electrode is configured to move from the first position to the second position when a force is applied to the end effector by a tissue section. The first electrode and the second electrode define a treatment area when the second electrode is in the second position.

5 Claims, 36 Drawing Sheets

(51) Int. Cl.
  *A61B 18/00* (2006.01)
  *A61B 90/00* (2016.01)
(52) U.S. Cl.
  CPC .. *A61B 18/1485* (2013.01); *A61B 2018/0013* (2013.01); *A61B 2018/0016* (2013.01); *A61B 2018/0063* (2013.01); *A61B 2018/0072* (2013.01); *A61B 2018/00077* (2013.01); *A61B 2018/00083* (2013.01); *A61B 2018/00101* (2013.01); *A61B 2018/00136* (2013.01); *A61B 2018/00148* (2013.01); *A61B 2018/00196* (2013.01); *A61B 2018/00214* (2013.01); *A61B 2018/00339* (2013.01); *A61B 2018/00559* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/00619* (2013.01); *A61B 2018/00648* (2013.01); *A61B 2018/00714* (2013.01); *A61B 2018/00732* (2013.01); *A61B 2018/00767* (2013.01); *A61B 2018/00791* (2013.01); *A61B 2018/00827* (2013.01); *A61B 2018/00892* (2013.01); *A61B 2018/00904* (2013.01); *A61B 2018/00952* (2013.01); *A61B 2018/00958* (2013.01); *A61B 2018/124* (2013.01); *A61B 2018/126* (2013.01); *A61B 2018/128* (2013.01); *A61B 2018/1226* (2013.01); *A61B 2018/1253* (2013.01); *A61B 2018/147* (2013.01); *A61B 2018/1407* (2013.01); *A61B 2018/1412* (2013.01); *A61B 2018/1455* (2013.01); *A61B 2018/1465* (2013.01); *A61B 2018/1467* (2013.01); *A61B 2018/1475* (2013.01); *A61B 2018/1495* (2013.01); *A61B 2090/065* (2016.02); *A61B 2090/0807* (2016.02)

(58) Field of Classification Search
  CPC ...... A61B 18/1485; A61B 2018/00196; A61B 2018/00589; A61B 2018/00595; A61B 2018/00607; A61B 2018/00619; A61B 2018/0063; A61B 2018/1455; A61B 2018/1452; A61B 2018/1465; A61B 2018/1467; A61B 2018/1495
  See application file for complete search history.

(56) References Cited

U.S. PATENT DOCUMENTS

| | | | |
|---|---|---|---|
| 2,510,693 A | 6/1950 | Green | |
| 3,166,971 A | 1/1965 | Stoecker | |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,463,759 A | 8/1984 | Garito et al. | |
| 4,492,231 A | 1/1985 | Auth | |
| 4,535,773 A | 8/1985 | Yoon | |
| 4,545,926 A | 10/1985 | Fouts, Jr. et al. | |
| 4,550,870 A | 11/1985 | Krumme et al. | |
| 4,582,236 A | 4/1986 | Hirose | |
| 4,617,927 A | 10/1986 | Manes | |
| 4,735,603 A | 4/1988 | Goodson et al. | |
| 4,761,871 A | 8/1988 | O'Connor et al. | |
| 4,830,462 A | 5/1989 | Karny et al. | |
| 4,849,133 A | 7/1989 | Yoshida et al. | |
| 4,860,745 A | 8/1989 | Farin et al. | |
| 4,878,493 A | 11/1989 | Pasternak et al. | |
| 4,910,389 A | 3/1990 | Sherman et al. | |
| 4,920,978 A * | 5/1990 | Colvin | A61N 1/403 |
| | | | 600/549 |
| 4,936,842 A | 6/1990 | D'Amelio et al. | |
| 5,061,269 A | 10/1991 | Muller | |
| 5,099,840 A | 3/1992 | Goble et al. | |
| 5,104,025 A | 4/1992 | Main et al. | |
| 5,106,538 A | 4/1992 | Barma et al. | |
| 5,108,383 A | 4/1992 | White | |
| 5,160,334 A | 11/1992 | Billings et al. | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,217,460 A | 6/1993 | Knoepfler | |
| 5,234,428 A | 8/1993 | Kaufman | |
| 5,258,006 A | 11/1993 | Rydell et al. | |
| 5,285,945 A | 2/1994 | Brinkerhoff et al. | |
| 5,290,286 A | 3/1994 | Parins | |
| 5,309,927 A | 5/1994 | Welch | |
| 5,318,564 A * | 6/1994 | Eggers | A61B 18/1233 |
| | | | 606/47 |
| 5,318,589 A | 6/1994 | Lichtman | |
| 5,330,471 A | 7/1994 | Eggers | |
| 5,339,723 A | 8/1994 | Huitema | |
| 5,342,359 A | 8/1994 | Rydell | |
| 5,361,583 A | 11/1994 | Huitema | |
| 5,383,874 A | 1/1995 | Jackson et al. | |
| 5,387,207 A | 2/1995 | Dyer et al. | |
| 5,389,098 A | 2/1995 | Tsuruta et al. | |
| 5,395,312 A | 3/1995 | Desai | |
| 5,395,363 A | 3/1995 | Billings et al. | |
| 5,395,364 A | 3/1995 | Anderhub et al. | |
| 5,396,900 A | 3/1995 | Slater et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,443,463 A | 8/1995 | Stern et al. | |
| 5,445,638 A | 8/1995 | Rydell et al. | |
| 5,451,227 A | 9/1995 | Michaelson | |
| 5,458,598 A | 10/1995 | Feinberg et al. | |
| 5,465,895 A | 11/1995 | Knodel et al. | |
| 5,472,443 A | 12/1995 | Cordis et al. | |
| 5,476,479 A | 12/1995 | Green et al. | |
| 5,480,409 A | 1/1996 | Riza | |
| 5,484,436 A | 1/1996 | Eggers et al. | |
| 5,486,189 A | 1/1996 | Mudry et al. | |
| 5,496,317 A | 3/1996 | Goble et al. | |
| 5,504,650 A | 4/1996 | Katsui et al. | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |
| 5,531,744 A | 7/1996 | Nardella et al. | |
| 5,542,916 A | 8/1996 | Hirsch et al. | |
| 5,558,671 A | 9/1996 | Yates | |
| 5,563,179 A | 10/1996 | Stone et al. | |
| 5,571,121 A | 11/1996 | Heifetz | |
| 5,573,534 A | 11/1996 | Stone | |
| 5,584,830 A | 12/1996 | Ladd et al. | |
| 5,599,350 A | 2/1997 | Schulze et al. | |
| 5,611,813 A | 3/1997 | Lichtman | |
| 5,618,307 A | 4/1997 | Donlon et al. | |
| 5,624,452 A | 4/1997 | Yates | |
| 5,647,871 A | 7/1997 | Levine et al. | |
| 5,658,281 A * | 8/1997 | Heard | A61B 18/1445 |
| | | | 606/41 |
| 5,662,667 A | 9/1997 | Knodel | |
| 5,665,085 A | 9/1997 | Nardella | |
| 5,665,100 A | 9/1997 | Yoon | |
| 5,674,219 A | 10/1997 | Monson et al. | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,713,896 A | 2/1998 | Nardella | |
| 5,716,366 A | 2/1998 | Yates | |

(56) References Cited

U.S. PATENT DOCUMENTS

| | | | |
|---|---|---|---|
| 5,735,848 A | 4/1998 | Yates et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,779,701 A | 7/1998 | McBrayer et al. | |
| 5,782,834 A | 7/1998 | Lucey et al. | |
| 5,792,138 A | 8/1998 | Shipp | |
| 5,797,941 A | 8/1998 | Schulze et al. | |
| 5,800,432 A | 9/1998 | Swanson | |
| 5,800,449 A | 9/1998 | Wales | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,093 A | 10/1998 | Williamson, IV et al. | |
| 5,836,909 A | 11/1998 | Cosmescu | |
| 5,836,943 A | 11/1998 | Miller, III | |
| 5,853,412 A | 12/1998 | Mayenberger | |
| 5,876,401 A | 3/1999 | Schulze et al. | |
| 5,880,668 A | 3/1999 | Hall | |
| 5,891,142 A | 4/1999 | Eggers et al. | |
| 5,906,625 A | 5/1999 | Bito et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A | 3/2000 | Goble | |
| 6,050,996 A * | 4/2000 | Schmaltz | A61B 18/14 606/50 |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A * | 7/2000 | Ingle | A61N 1/403 606/41 |
| 6,099,483 A | 8/2000 | Palmer et al. | |
| 6,099,550 A | 8/2000 | Yoon | |
| H1904 H | 10/2000 | Yates et al. | |
| 6,144,402 A | 11/2000 | Norsworthy et al. | |
| 6,152,923 A | 11/2000 | Ryan | |
| 6,174,309 B1 | 1/2001 | Wrublewski et al. | |
| 6,176,857 B1 * | 1/2001 | Ashley | A61B 18/08 606/32 |
| 6,206,876 B1 | 3/2001 | Levine et al. | |
| 6,228,080 B1 | 5/2001 | Gines | |
| 6,259,230 B1 | 7/2001 | Chou | |
| 6,277,117 B1 | 8/2001 | Tetzlaff et al. | |
| 6,292,700 B1 | 9/2001 | Morrison et al. | |
| 6,325,799 B1 | 12/2001 | Goble | |
| 6,340,878 B1 | 1/2002 | Oglesbee | |
| 6,391,026 B1 * | 5/2002 | Hung | A61B 18/00 606/13 |
| 6,398,779 B1 | 6/2002 | Buysse et al. | |
| H2037 H | 7/2002 | Yates et al. | |
| 6,419,675 B1 | 7/2002 | Gallo, Sr. | |
| 6,430,446 B1 | 8/2002 | Knowlton | |
| 6,443,968 B1 | 9/2002 | Holthaus et al. | |
| 6,458,128 B1 | 10/2002 | Schulze | |
| 6,464,702 B2 | 10/2002 | Schulze et al. | |
| 6,491,690 B1 | 12/2002 | Goble et al. | |
| 6,500,112 B1 | 12/2002 | Khouri | |
| 6,500,176 B1 | 12/2002 | Truckai et al. | |
| 6,503,248 B1 | 1/2003 | Levine | |
| 6,511,480 B1 | 1/2003 | Tetzlaff et al. | |
| 6,514,252 B2 | 2/2003 | Nezhat et al. | |
| 6,517,565 B1 | 2/2003 | Whitman et al. | |
| 6,531,846 B1 | 3/2003 | Smith | |
| 6,533,784 B2 | 3/2003 | Truckai et al. | |
| 6,537,272 B2 | 3/2003 | Christopherson et al. | |
| 6,554,829 B2 | 4/2003 | Schulze et al. | |
| 6,558,376 B2 | 5/2003 | Bishop | |
| 6,572,639 B1 | 6/2003 | Ingle et al. | |
| 6,575,969 B1 | 6/2003 | Rittman, III et al. | |
| 6,584,360 B2 | 6/2003 | Francischelli et al. | |
| 6,585,735 B1 | 7/2003 | Frazier et al. | |
| 6,589,200 B1 | 7/2003 | Schwemberger et al. | |
| 6,602,252 B2 | 8/2003 | Mollenauer | |
| 6,620,161 B2 | 9/2003 | Schulze et al. | |
| 6,622,731 B2 | 9/2003 | Daniel et al. | |
| 6,623,482 B2 | 9/2003 | Pendekanti et al. | |
| 6,635,057 B2 | 10/2003 | Harano et al. | |
| 6,651,669 B1 | 11/2003 | Burnside | |
| 6,656,177 B2 | 12/2003 | Truckai et al. | |
| 6,656,198 B2 | 12/2003 | Tsonton et al. | |
| 6,673,248 B2 | 1/2004 | Chowdhury | |
| 6,679,882 B1 | 1/2004 | Kornerup | |
| 6,695,840 B2 | 2/2004 | Schulze | |
| 6,722,552 B2 | 4/2004 | Fenton, Jr. | |
| 6,770,072 B1 | 8/2004 | Truckai et al. | |
| 6,773,409 B2 | 8/2004 | Truckai et al. | |
| 6,773,435 B2 | 8/2004 | Schulze et al. | |
| 6,775,575 B2 | 8/2004 | Bommannan et al. | |
| 6,789,939 B2 | 9/2004 | Schrödinger et al. | |
| 6,796,981 B2 | 9/2004 | Wham et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,835,199 B2 | 12/2004 | McGuckin, Jr. et al. | |
| 6,840,938 B1 | 1/2005 | Morley et al. | |
| 6,860,880 B2 | 3/2005 | Treat et al. | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 7,000,818 B2 | 2/2006 | Shelton, IV et al. | |
| 7,011,657 B2 | 3/2006 | Truckai et al. | |
| 7,041,102 B2 | 5/2006 | Truckai et al. | |
| 7,055,731 B2 | 6/2006 | Shelton, IV et al. | |
| 7,063,699 B2 | 6/2006 | Hess et al. | |
| 7,066,936 B2 | 6/2006 | Ryan | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,087,054 B2 | 8/2006 | Truckai et al. | |
| 7,094,235 B2 | 8/2006 | Francischelli et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,112,201 B2 | 9/2006 | Truckai et al. | |
| 7,118,570 B2 | 10/2006 | Tetzlaff et al. | |
| 7,125,409 B2 | 10/2006 | Truckai et al. | |
| 7,131,970 B2 | 11/2006 | Moses et al. | |
| 7,137,980 B2 | 11/2006 | Buysse et al. | |
| 7,143,925 B2 | 12/2006 | Shelton, IV et al. | |
| 7,147,138 B2 | 12/2006 | Shelton, IV | |
| 7,156,846 B2 | 1/2007 | Dycus et al. | |
| 7,160,296 B2 | 1/2007 | Pearson et al. | |
| 7,169,146 B2 | 1/2007 | Truckai et al. | |
| 7,169,156 B2 | 1/2007 | Hart | |
| 7,186,253 B2 | 3/2007 | Truckai et al. | |
| 7,189,233 B2 | 3/2007 | Truckai et al. | |
| 7,195,631 B2 | 3/2007 | Dumbauld | |
| 7,207,471 B2 | 4/2007 | Heinrich et al. | |
| 7,220,951 B2 | 5/2007 | Truckai et al. | |
| 7,225,964 B2 | 6/2007 | Mastri et al. | |
| 7,226,448 B2 | 6/2007 | Bertolero et al. | |
| 7,232,440 B2 | 6/2007 | Dumbauld et al. | |
| 7,235,073 B2 | 6/2007 | Levine et al. | |
| 7,241,294 B2 | 7/2007 | Reschke | |
| 7,251,531 B2 | 7/2007 | Mosher et al. | |
| 7,252,667 B2 | 8/2007 | Moses et al. | |
| 7,267,677 B2 | 9/2007 | Johnson et al. | |
| 7,267,685 B2 | 9/2007 | Butaric et al. | |
| 7,287,682 B1 | 10/2007 | Ezzat et al. | |
| 7,300,450 B2 | 11/2007 | Vleugels et al. | |
| 7,303,557 B2 | 12/2007 | Wham et al. | |
| 7,307,313 B2 | 12/2007 | Ohyanagi et al. | |
| 7,309,849 B2 | 12/2007 | Truckai et al. | |
| 7,311,709 B2 | 12/2007 | Truckai et al. | |

(56) References Cited

U.S. PATENT DOCUMENTS

| | | | |
|---|---|---|---|
| 7,329,257 B2 * | 2/2008 | Kanehira | A61B 17/3201 606/45 |
| 7,354,440 B2 | 4/2008 | Truckal et al. | |
| 7,357,287 B2 | 4/2008 | Shelton, IV et al. | |
| 7,364,577 B2 | 4/2008 | Wham et al. | |
| 7,367,976 B2 | 5/2008 | Lawes et al. | |
| 7,371,227 B2 | 5/2008 | Zeiner | |
| RE40,388 E | 6/2008 | Gines | |
| 7,381,209 B2 | 6/2008 | Truckai et al. | |
| 7,384,420 B2 | 6/2008 | Dycus et al. | |
| 7,396,356 B2 | 7/2008 | Mollenauer | |
| 7,403,224 B2 | 7/2008 | Fuller et al. | |
| 7,404,508 B2 | 7/2008 | Smith et al. | |
| 7,407,077 B2 | 8/2008 | Ortiz et al. | |
| 7,422,139 B2 | 9/2008 | Shelton, IV et al. | |
| 7,435,582 B2 | 10/2008 | Zimmermann et al. | |
| 7,442,193 B2 * | 10/2008 | Shields | A61B 18/1445 606/49 |
| 7,445,621 B2 | 11/2008 | Dumbauld et al. | |
| 7,464,846 B2 | 12/2008 | Shelton, IV et al. | |
| 7,473,253 B2 | 1/2009 | Dycus et al. | |
| 7,488,319 B2 | 2/2009 | Yates | |
| 7,491,201 B2 | 2/2009 | Shields et al. | |
| 7,494,501 B2 | 2/2009 | Ahlberg et al. | |
| 7,498,080 B2 | 3/2009 | Tung et al. | |
| 7,510,107 B2 | 3/2009 | Timm et al. | |
| 7,513,025 B2 | 4/2009 | Fischer | |
| 7,517,349 B2 | 4/2009 | Truckai et al. | |
| 7,540,872 B2 | 6/2009 | Schechter et al. | |
| 7,550,216 B2 | 6/2009 | Ofer et al. | |
| 7,559,452 B2 | 7/2009 | Wales et al. | |
| 7,582,086 B2 | 9/2009 | Privitera et al. | |
| 7,586,289 B2 | 9/2009 | Andruk et al. | |
| 7,588,176 B2 | 9/2009 | Timm et al. | |
| 7,594,925 B2 | 9/2009 | Danek et al. | |
| 7,597,693 B2 | 10/2009 | Garrison | |
| 7,604,150 B2 | 10/2009 | Boudreaux | |
| 7,628,791 B2 | 12/2009 | Garrison et al. | |
| 7,628,792 B2 | 12/2009 | Guerra | |
| 7,632,269 B2 | 12/2009 | Truckai et al. | |
| 7,641,653 B2 * | 1/2010 | Dalla Betta | A61B 18/1442 200/293.1 |
| 7,641,671 B2 | 1/2010 | Crainich | |
| 7,644,848 B2 | 1/2010 | Swayze et al. | |
| 7,645,277 B2 | 1/2010 | McClurken et al. | |
| 7,648,499 B2 | 1/2010 | Orszulak et al. | |
| 7,658,311 B2 | 2/2010 | Boudreaux | |
| 7,665,647 B2 | 2/2010 | Shelton, IV et al. | |
| 7,666,206 B2 | 2/2010 | Taniguchi et al. | |
| 7,703,459 B2 | 4/2010 | Saadat et al. | |
| 7,708,751 B2 | 5/2010 | Hughes et al. | |
| 7,722,607 B2 | 5/2010 | Dumbauld et al. | |
| 7,753,904 B2 | 7/2010 | Shelton, IV et al. | |
| 7,753,908 B2 * | 7/2010 | Swanson | A61B 18/1445 606/49 |
| 7,762,445 B2 | 7/2010 | Heinrich et al. | |
| 7,766,910 B2 | 8/2010 | Hixson et al. | |
| 7,776,037 B2 | 8/2010 | Odom | |
| 7,780,663 B2 | 8/2010 | Yates et al. | |
| 7,784,663 B2 | 8/2010 | Shelton, IV | |
| 7,803,156 B2 | 9/2010 | Eder et al. | |
| 7,815,641 B2 | 10/2010 | Dodde et al. | |
| 7,819,298 B2 | 10/2010 | Hall et al. | |
| 7,819,299 B2 | 10/2010 | Sheltoin, IV et al. | |
| 7,832,408 B2 | 11/2010 | Shelton, IV et al. | |
| 7,832,612 B2 | 11/2010 | Baxter, III et al. | |
| 7,846,159 B2 | 12/2010 | Morrison et al. | |
| 7,879,035 B2 | 2/2011 | Garrison et al. | |
| 7,879,070 B2 | 2/2011 | Ortiz et al. | |
| 7,901,400 B2 | 3/2011 | Wham et al. | |
| 7,931,649 B2 | 4/2011 | Couture et al. | |
| 7,935,114 B2 | 5/2011 | Takashino et al. | |
| 7,955,331 B2 | 6/2011 | Truckai et al. | |
| 7,963,963 B2 | 6/2011 | Francischelli et al. | |
| 7,967,602 B2 | 6/2011 | Lindquist | |
| 7,981,113 B2 | 7/2011 | Truckai et al. | |
| 7,997,278 B2 | 8/2011 | Utley et al. | |
| 8,020,743 B2 | 9/2011 | Shelton, IV | |
| 8,058,771 B2 | 11/2011 | Giordano et al. | |
| 8,070,036 B1 | 12/2011 | Knodel et al. | |
| 8,105,323 B2 | 1/2012 | Buysse et al. | |
| 8,128,624 B2 | 3/2012 | Couture et al. | |
| 8,136,712 B2 | 3/2012 | Zingman | |
| 8,141,762 B2 | 3/2012 | Bedi et al. | |
| 8,157,145 B2 | 4/2012 | Shelton, IV et al. | |
| 8,197,472 B2 | 6/2012 | Lau et al. | |
| 8,197,479 B2 | 6/2012 | Olson et al. | |
| 8,221,415 B2 | 7/2012 | Francischelli | |
| 8,246,615 B2 | 8/2012 | Behnke | |
| 8,246,618 B2 | 8/2012 | Bucciaglia et al. | |
| 8,251,994 B2 | 8/2012 | McKenna et al. | |
| 8,262,563 B2 | 9/2012 | Bakos et al. | |
| 8,277,446 B2 | 10/2012 | Heard | |
| 8,277,447 B2 | 10/2012 | Garrison et al. | |
| 8,282,669 B2 | 10/2012 | Gerber et al. | |
| 8,287,528 B2 | 10/2012 | Wham et al. | |
| 8,292,886 B2 | 10/2012 | Kerr et al. | |
| 8,298,232 B2 | 10/2012 | Unger | |
| 8,303,583 B2 | 11/2012 | Hosier et al. | |
| 8,323,310 B2 | 12/2012 | Kingsley | |
| 8,377,059 B2 | 2/2013 | Deville et al. | |
| 8,397,971 B2 | 3/2013 | Yates et al. | |
| 8,414,577 B2 | 4/2013 | Boudreaux et al. | |
| 8,430,876 B2 | 4/2013 | Kappus et al. | |
| 8,453,906 B2 | 6/2013 | Huang et al. | |
| 8,460,288 B2 | 6/2013 | Tamai et al. | |
| 8,460,292 B2 | 6/2013 | Truckai et al. | |
| 8,486,057 B2 | 7/2013 | Behnke, II | |
| 8,496,682 B2 | 7/2013 | Guerra et al. | |
| 8,535,311 B2 | 9/2013 | Schall | |
| 8,562,598 B2 | 10/2013 | Falkenstein et al. | |
| 8,562,604 B2 | 10/2013 | Nishimura | |
| 8,568,412 B2 | 10/2013 | Brandt et al. | |
| 8,569,997 B2 | 10/2013 | Lee | |
| 8,574,231 B2 | 11/2013 | Boudreaux et al. | |
| 8,591,506 B2 | 11/2013 | Wham et al. | |
| 8,613,383 B2 | 12/2013 | Beckman et al. | |
| 8,623,044 B2 | 1/2014 | Timm et al. | |
| 8,628,529 B2 | 1/2014 | Aldridge et al. | |
| 8,632,461 B2 | 1/2014 | Glossop | |
| 8,647,350 B2 | 2/2014 | Mohan et al. | |
| 8,685,020 B2 | 4/2014 | Weizman et al. | |
| 8,696,665 B2 | 4/2014 | Hunt et al. | |
| 8,702,704 B2 | 4/2014 | Shelton, IV et al. | |
| 8,709,035 B2 | 4/2014 | Johnson et al. | |
| 8,715,270 B2 | 5/2014 | Weitzner et al. | |
| 8,715,277 B2 | 5/2014 | Weizman | |
| 8,734,443 B2 | 5/2014 | Hixson et al. | |
| 8,747,404 B2 | 6/2014 | Boudreaux et al. | |
| 8,753,338 B2 | 6/2014 | Widenhouse et al. | |
| 8,764,747 B2 | 7/2014 | Cummings et al. | |
| 8,790,342 B2 | 7/2014 | Stulen et al. | |
| 8,795,276 B2 | 8/2014 | Dietz et al. | |
| 8,795,327 B2 | 8/2014 | Dietz et al. | |
| 8,834,466 B2 | 9/2014 | Cummings et al. | |
| 8,834,518 B2 | 9/2014 | Faller et al. | |
| 8,888,776 B2 | 11/2014 | Dietz et al. | |
| 8,906,016 B2 | 12/2014 | Boudreaux et al. | |
| 8,926,607 B2 | 1/2015 | Norvell et al. | |
| 8,926,608 B2 | 1/2015 | Bacher et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,979,843 B2 | 3/2015 | Timm et al. | |
| 8,979,844 B2 | 3/2015 | White et al. | |
| 8,986,302 B2 | 3/2015 | Aldridge et al. | |
| 9,005,199 B2 | 4/2015 | Beckman et al. | |
| 9,011,437 B2 | 4/2015 | Woodruff et al. | |
| 9,044,243 B2 | 6/2015 | Johnson et al. | |
| 2002/0022836 A1 | 2/2002 | Goble et al. | |
| 2002/0165541 A1 | 11/2002 | Whitman | |
| 2003/0014053 A1 | 1/2003 | Nguyen et al. | |
| 2003/0105474 A1 | 6/2003 | Bonutti | |

(56) References Cited

U.S. PATENT DOCUMENTS

| | | |
|---|---|---|
| 2003/0109876 A1* | 6/2003 | Yamauchi .......... A61B 18/1442 606/48 |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1* | 9/2006 | Couture ............. A61B 18/1442 606/51 |
| 2006/0270916 A1 | 11/2006 | Skwarek et al. |
| 2006/0293656 A1 | 12/2006 | Shadduck et al. |
| 2007/0010808 A1* | 1/2007 | Dahla ................. A61B 18/14 606/41 |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0154256 A1* | 6/2008 | Payne ................ A61B 17/42 606/34 |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0030312 A1* | 1/2009 | Hadjicostis .......... A61B 8/12 600/439 |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022527 A1 | 1/2012 | Woodruff et al. |
| 2012/0059371 A1* | 3/2012 | Anderson .......... A61B 18/1445 606/45 |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1 | 5/2012 | Yates et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |

(56) References Cited

U.S. PATENT DOCUMENTS

| | | |
|---|---|---|
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 81/03272 A1 | 11/1981 |
| WO | WO 93/07817 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |

OTHER PUBLICATIONS

Written Opinion for PCT/US2014/052505, dated Mar. 30, 2015 (11 pages).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

(56) References Cited

OTHER PUBLICATIONS

Gibson, "Magnetic Refrigerator Successfully Tested," U.S. Department of Energy Research News, accessed online on Aug. 6, 2010 at http://www.eurekalerf.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
U.S. Appl. No. 14/227,699, filed Mar. 27, 2014.
U.S. Appl. No. 14/227,708, filed Mar. 27, 2014.
U.S. Appl. No. 14/032,391, filed Sep. 20, 2013.
U.S. Appl. No. 14/218,558, filed Mar. 18, 2014.
International Preliminary Report on Patentability for PCT/US2014/052505, dated Mar. 15, 2016 (12 pages).

\* cited by examiner

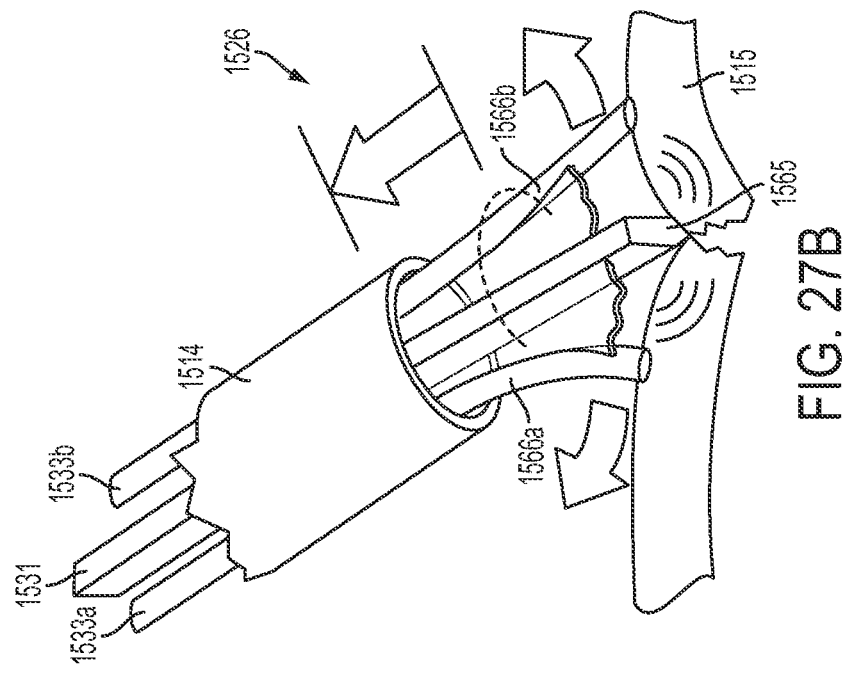
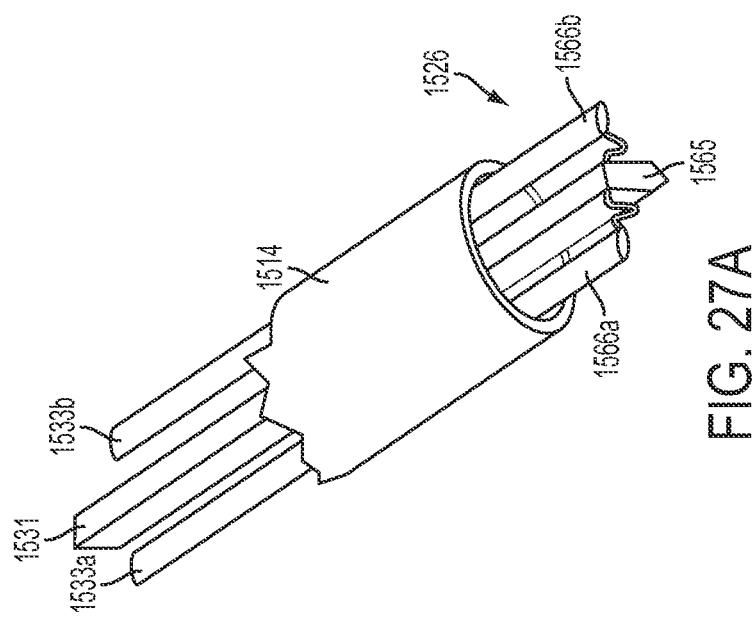

ELECTROSURGICAL (RF) MEDICAL INSTRUMENTS FOR CUTTING AND COAGULATING TISSUE

BACKGROUND

Electrosurgical devices are used in many surgical operations. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 100 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

SUMMARY

In various embodiments, an electrosurgical (RF) device is provided. The electrosurgical device comprises a handle, a shaft extending distally from the handle, and an end effector coupled to a distal end of the shaft. The end effector comprises a first electrode and a second electrode. The second electrode comprises a first position and a second position. The second electrode is configured to move from the first position to the second position when a force is applied to the end effector by a tissue section. The first electrode and the second electrode define a treatment area when the second electrode is in the second position.

In various embodiments, a base cap configured to interface with an electrosurgical instrument is provided. The base cap comprises an electrode layer configured to provide electrosurgical signals to a tissue section in contact with the base cap, a heat sink layer configured to prevent heat transfer between the base cap and the electrosurgical instrument, and sealing layer configured to seal the base cap. The base cap is removably coupled to the electrosurgical instrument.

In various embodiments, an electrosurgical (RF) device is provided. The electrosurgical device comprises a waveform generator configured to produce an electrosurgical signal comprising at least a first phase and a second phase, a first conductor configured to receive the first phase of the electrosurgical signal, and a second conductor configured to receive the second phase of the electrosurgical signal.

In various embodiments, an electrosurgical (RF) instrument is provided. The electrosurgical instrument comprises a handle, a shaft extending distally from the handle, and an end effector coupled to the distal end of the shaft. The end effector comprises a first jaw member comprising a first electrode and a second jaw member comprising a second electrode, wherein the first and second electrodes comprise a fluoropolymer material comprising an electrically conductive mica additive.

In various embodiments, a bipolar temperature controlled tissue ablation surgical device is provided. The surgical device comprises a handle, a shaft extending distally from the handle, and an end effector coupled to a distal end of the shaft. The end effector comprises a source electrode comprising a positive temperature controlled (PTC) material and a return electrode electrically isolated from the source electrode, wherein the source electrode and the return electrode are configured to receive a bipolar electrosurgical signal.

In various embodiments, an electrosurgical (RF) device is provided. The electrosurgical device comprises a handle, a shaft extending distally from the handle, and an end effector coupled to a distal end of the handle. The end effector comprises an upper jaw comprising a first electrode, a lower jaw comprising a second electrode, and a power tip extending from a distal end of the lower jaw. The power tip comprises an electrode configured to receive electrosurgical energy.

In various embodiments, a monopolar add-on for an electrosurgical device comprising a power tip is provided. The monopolar add-on comprises a handle configured to interface with a shaft of the electrosurgical device and a slip ring coupled to the handle. The slip ring is configured to interface with a conductor disposed within the shaft of the electrosurgical device. The conductor is coupled to a power tip located at the distal end of the electrosurgical instrument. The monopolar add-on further comprises a cable coupled to the slip ring. The cable is configured to couple to a monopolar generator. The monopolar add-on further comprises a switch configured to control delivery of a monopolar electrosurgical signal from the monopolar generator to the power tip.

FIGURES

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 10B is a detailed view of a section of the molded base cap shown in FIG. 10A.

Figure 1:
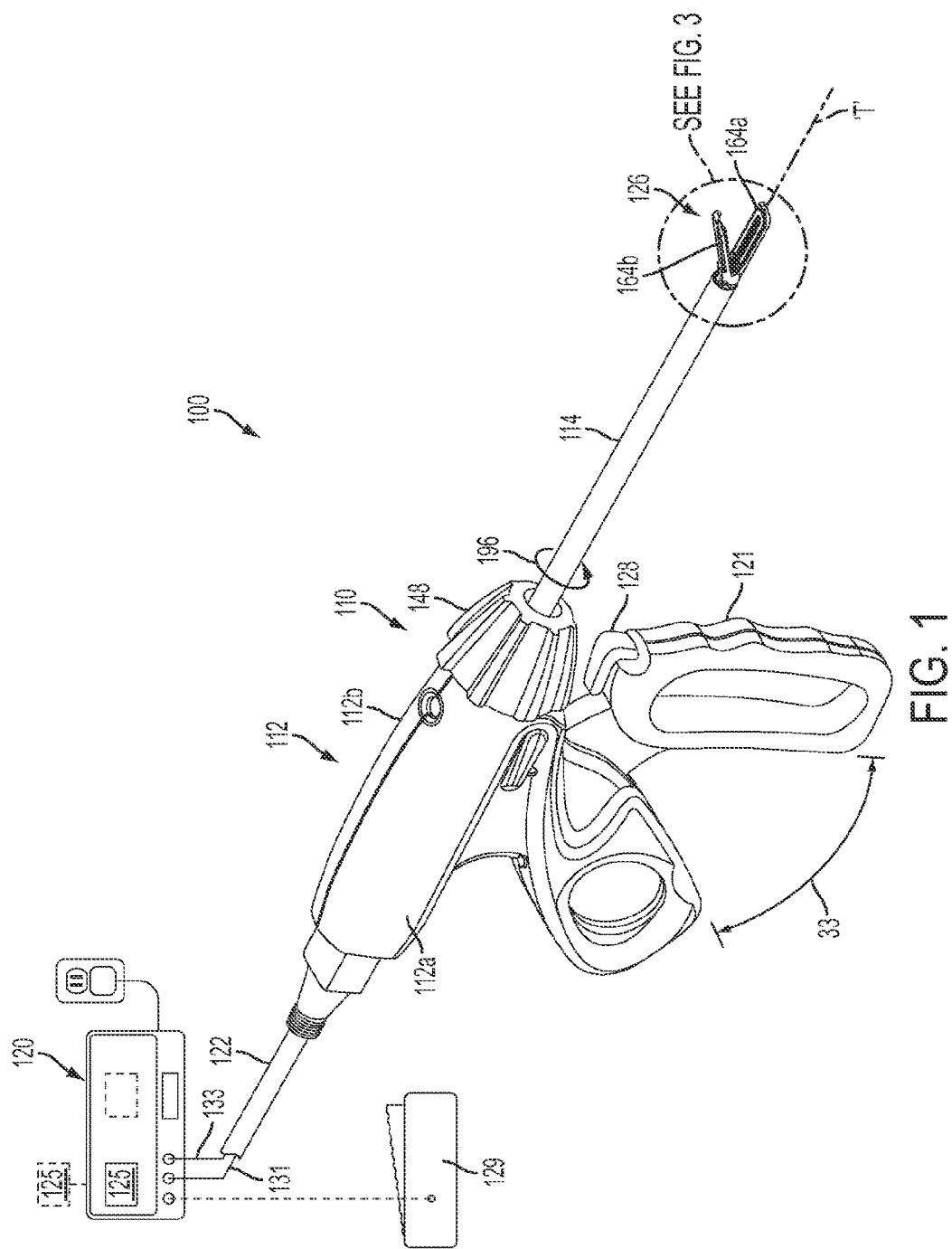
FIG. 1 illustrates a perspective view of one embodiment of an electrical energy surgical instrument.
Figure 7:
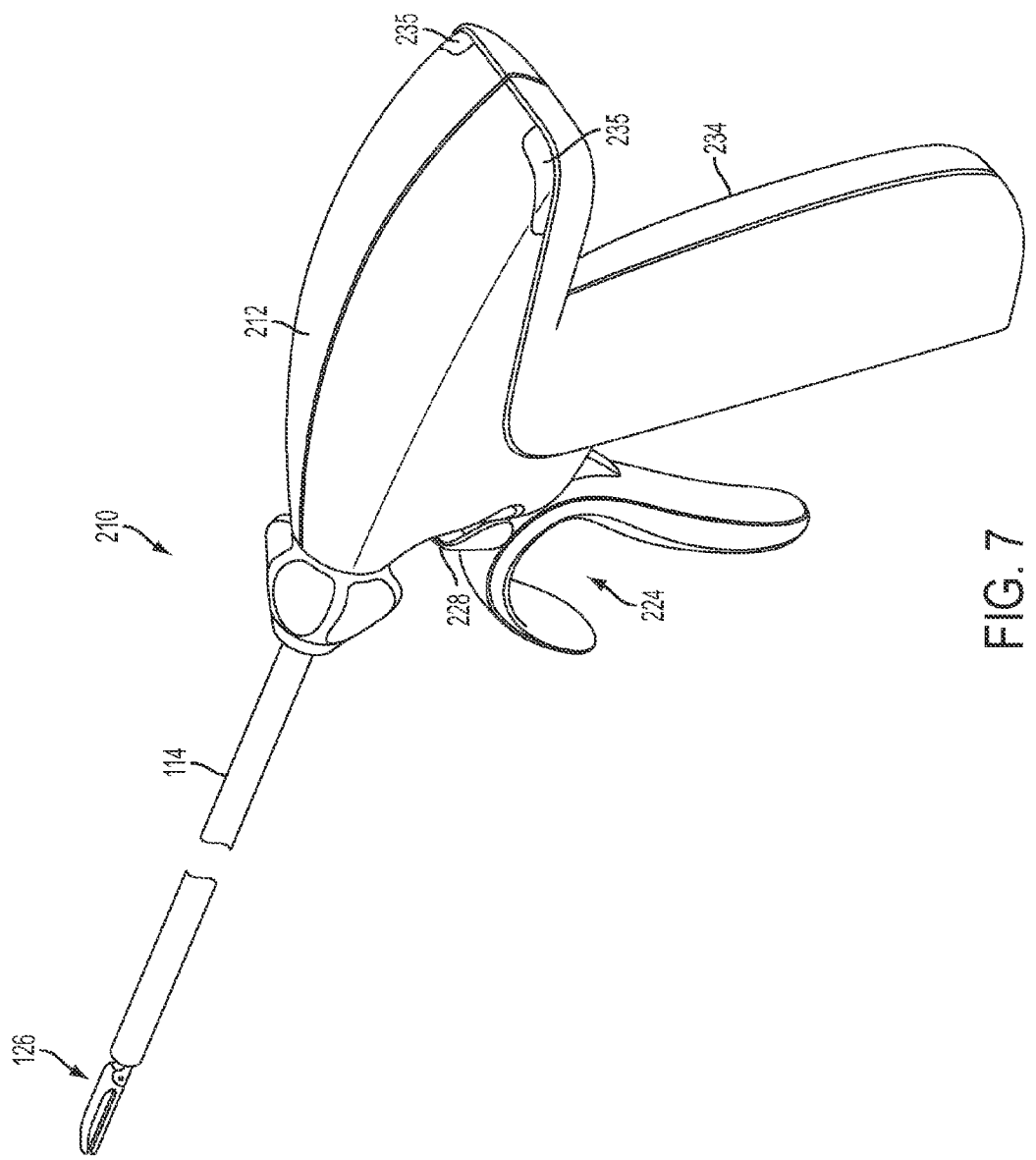
FIG. 7 illustrates a perspective view of one embodiment of a cordless electrical energy surgical instrument.
Figure 16A:
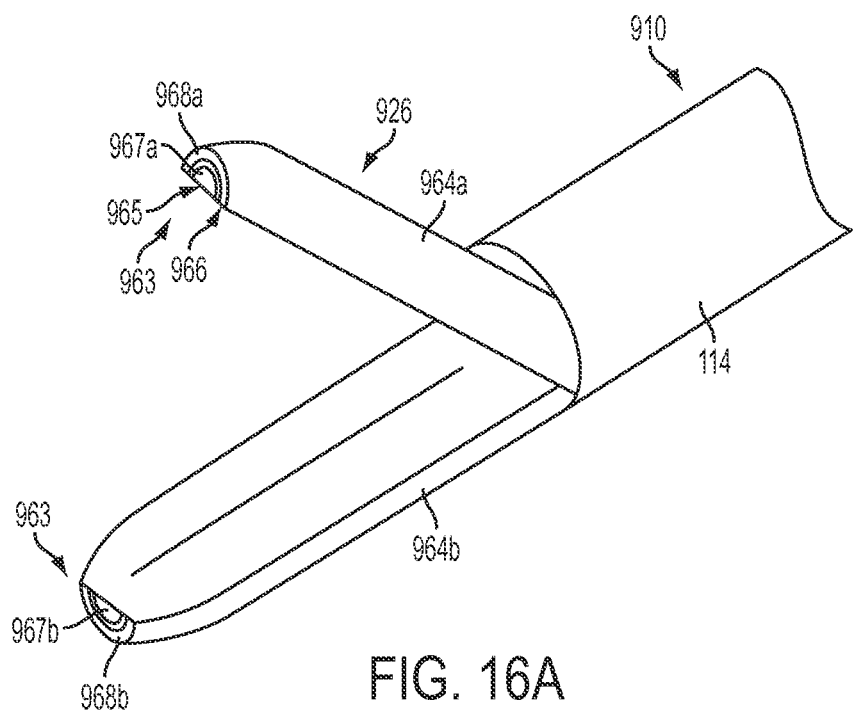
Figure 16B:
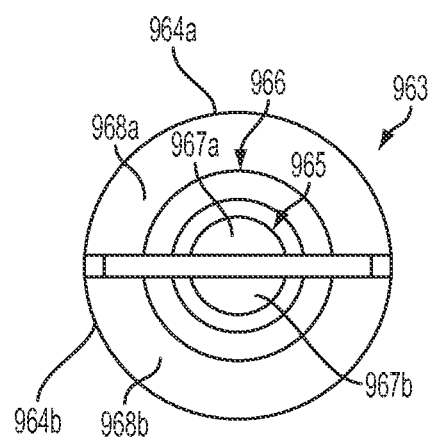

FIGS. 16A and 16B illustrate one embodiment of a surgical instrument, such as the surgical instrument shown in FIGS. 1 and 7, comprising an end effector where the end effector comprises a tissue ablation tip and where FIG. 16A illustrates a perspective view of the end effector with a jaw member in an open position and FIG. 16B illustrates an end view of the end effector with the jaw members in a closed position.

Figure 17:
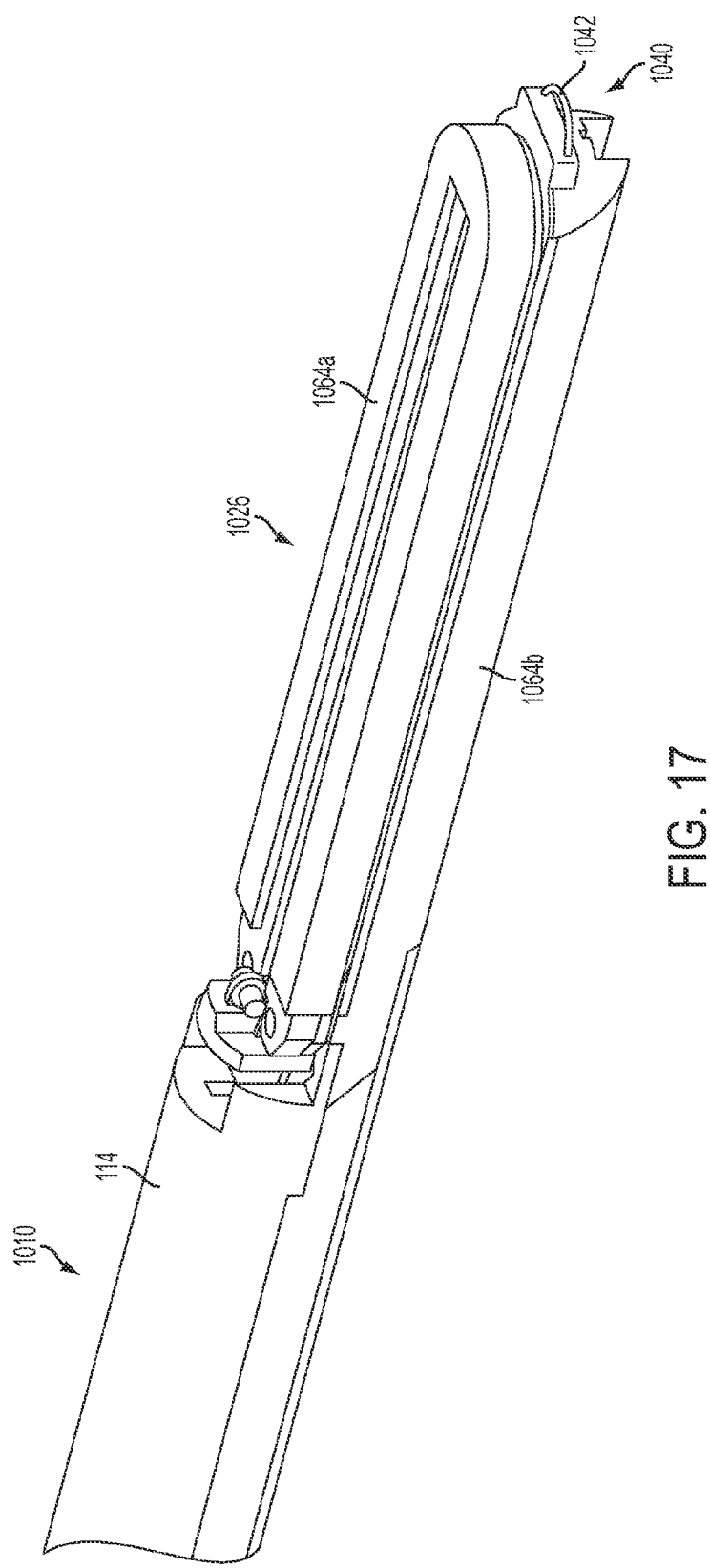

FIG. 17 illustrates one embodiment of an end effector for an electrosurgical device comprising a power tip.

Figure 18:
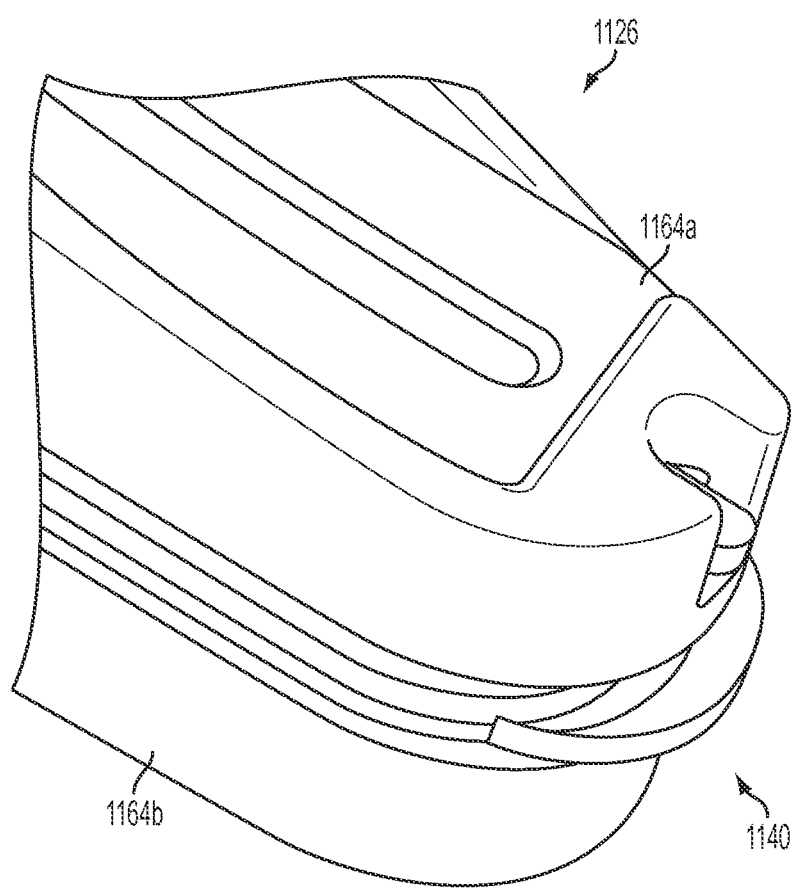

FIG. 18 illustrates one embodiment of the end effector of FIG. 17 comprising a half-circle power tip.

Figure 19:
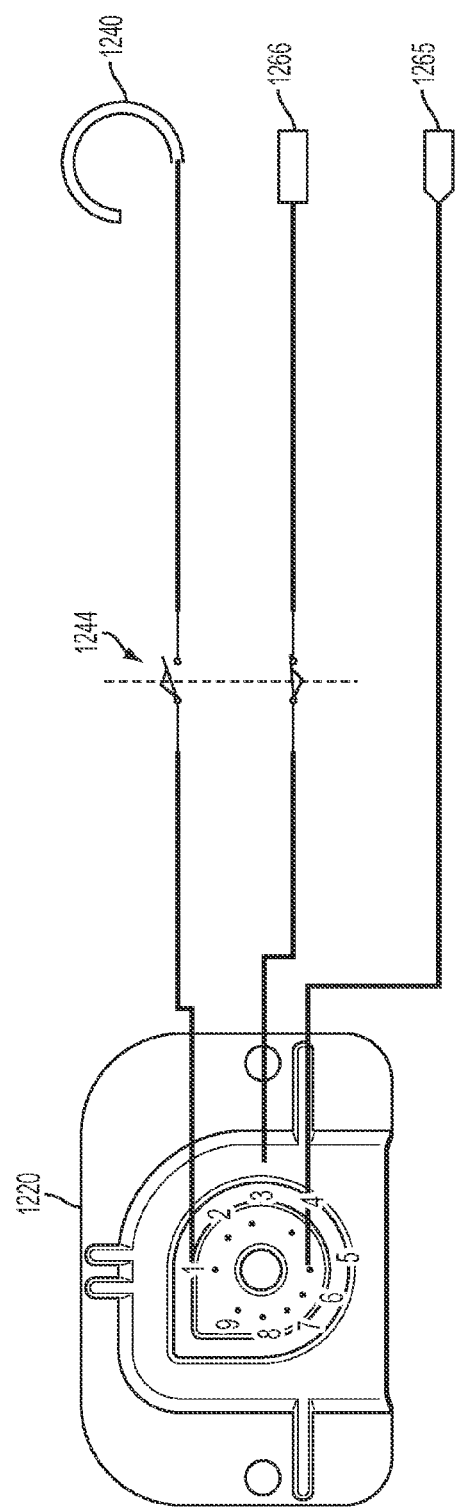

FIG. 19 illustrates one embodiment of an electrical connection between a generator, a power tip, a ground electrode, and a plurality of electrodes disposed within a clamp jaw end effector.

Figure 20:
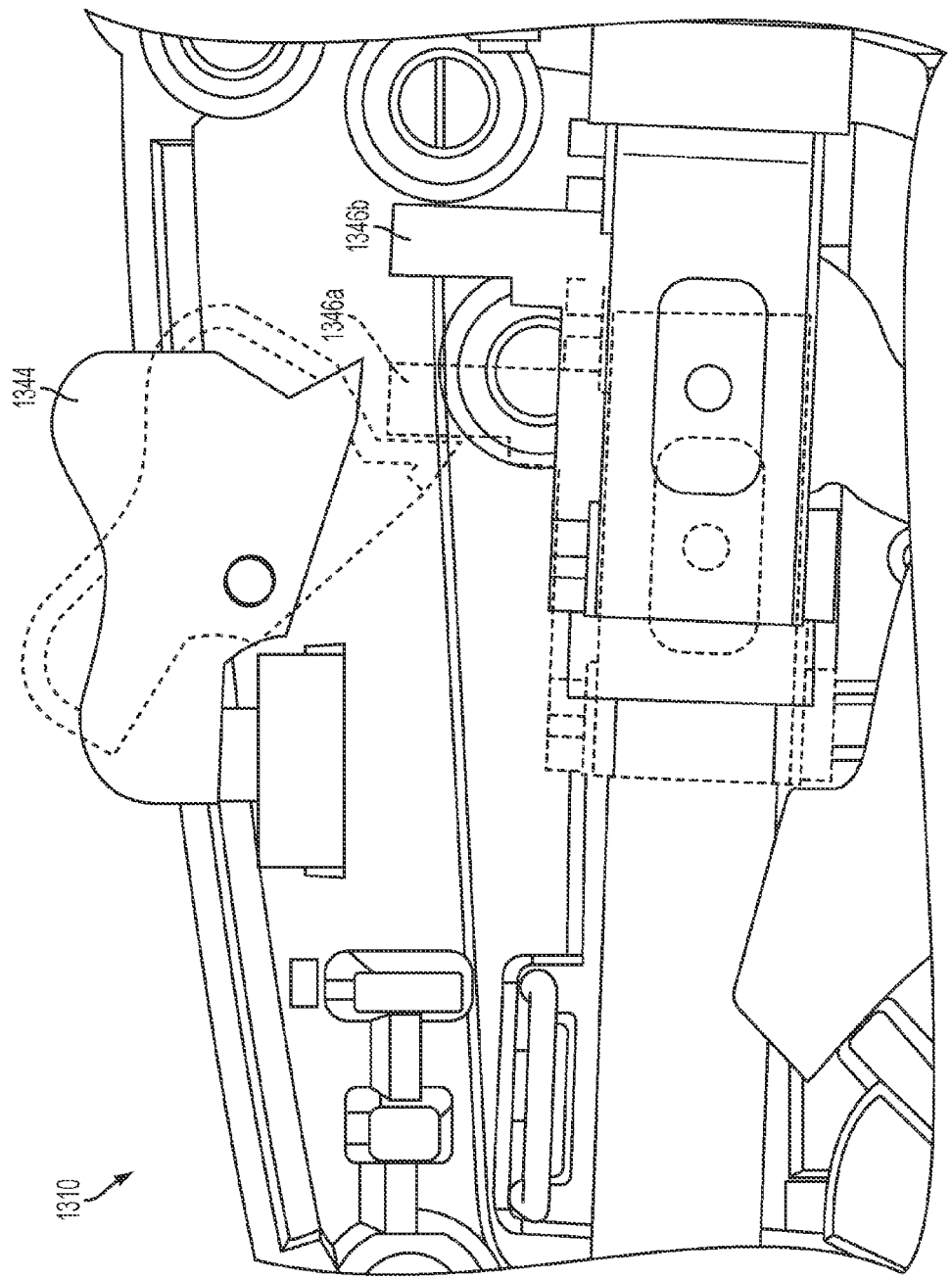

FIG. 20 illustrates one embodiment of a two-pole switch configured to control operation of a power tip, such as the power tip of FIG. 17.

Figure 21:
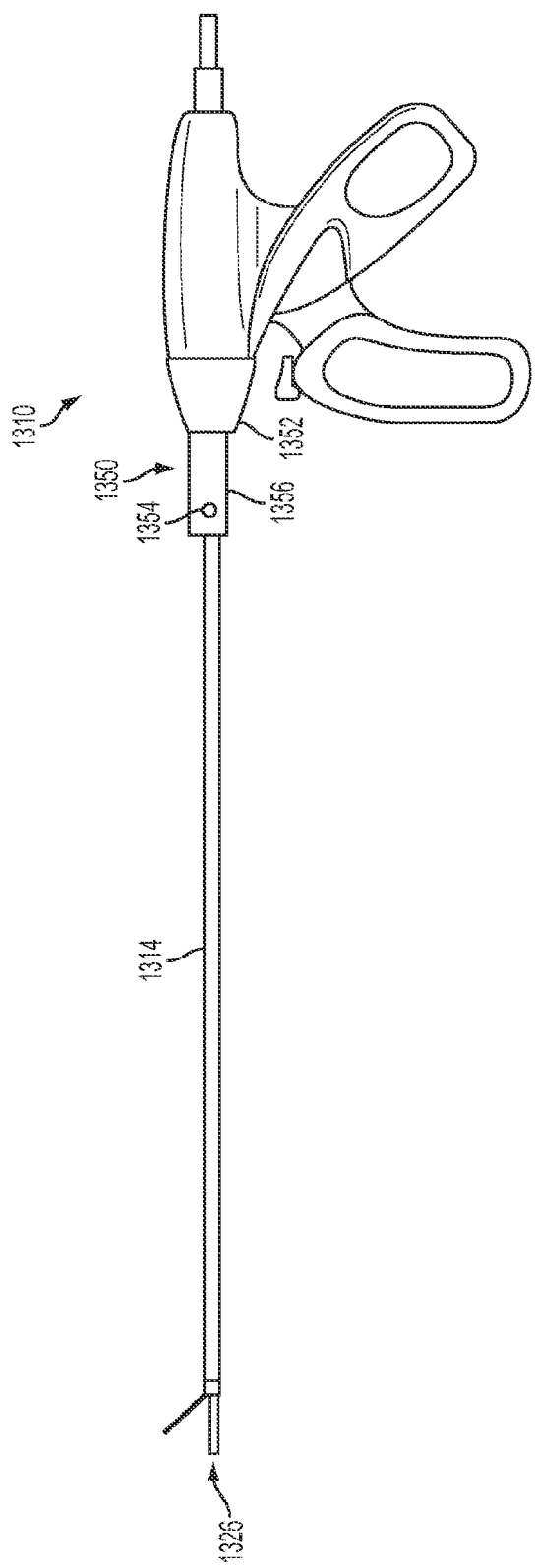
Figure 22:
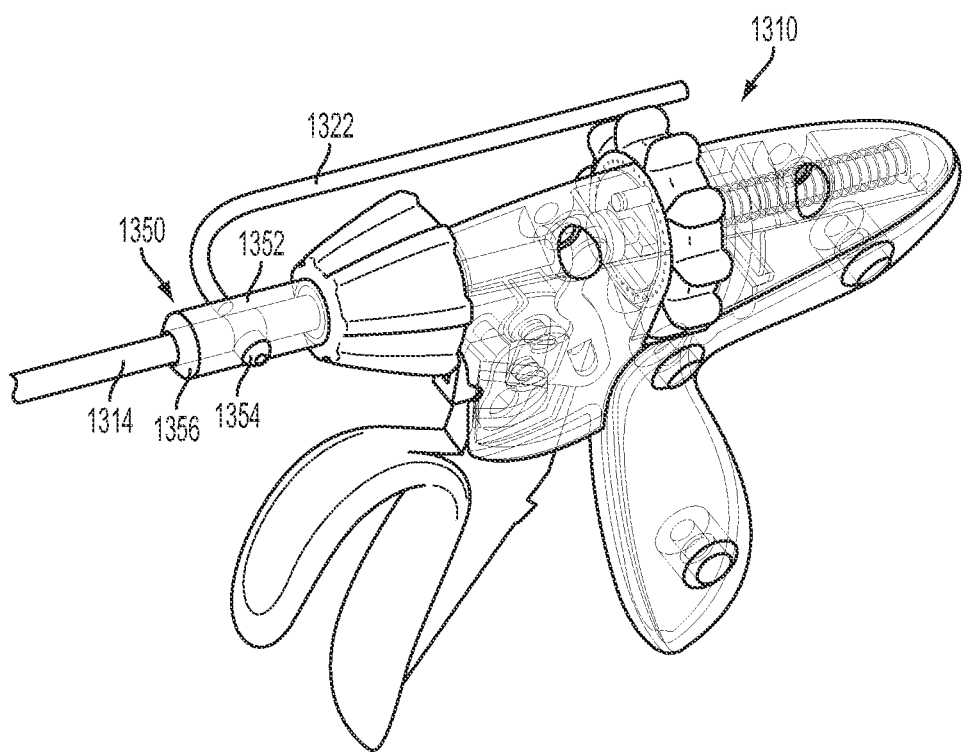

FIGS. 21 and 22 illustrate one embodiment of an electrosurgical device comprising a power tip configured to receive a monopolar add-on device.

Figure 23A:
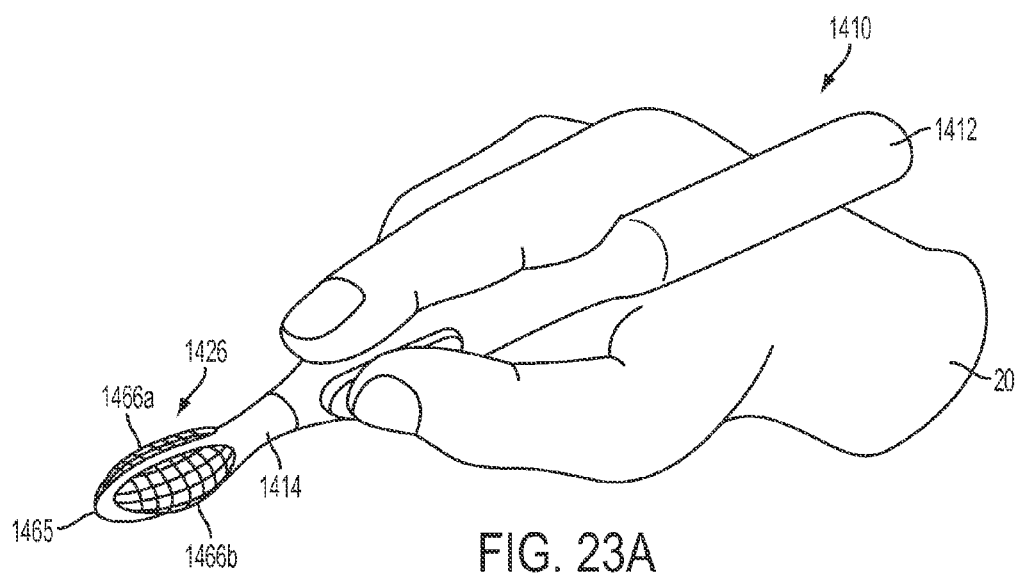

FIG. 23A illustrates one embodiment of a cordless electrosurgical instrument comprising a pencil grip handle.

Figure 23B:
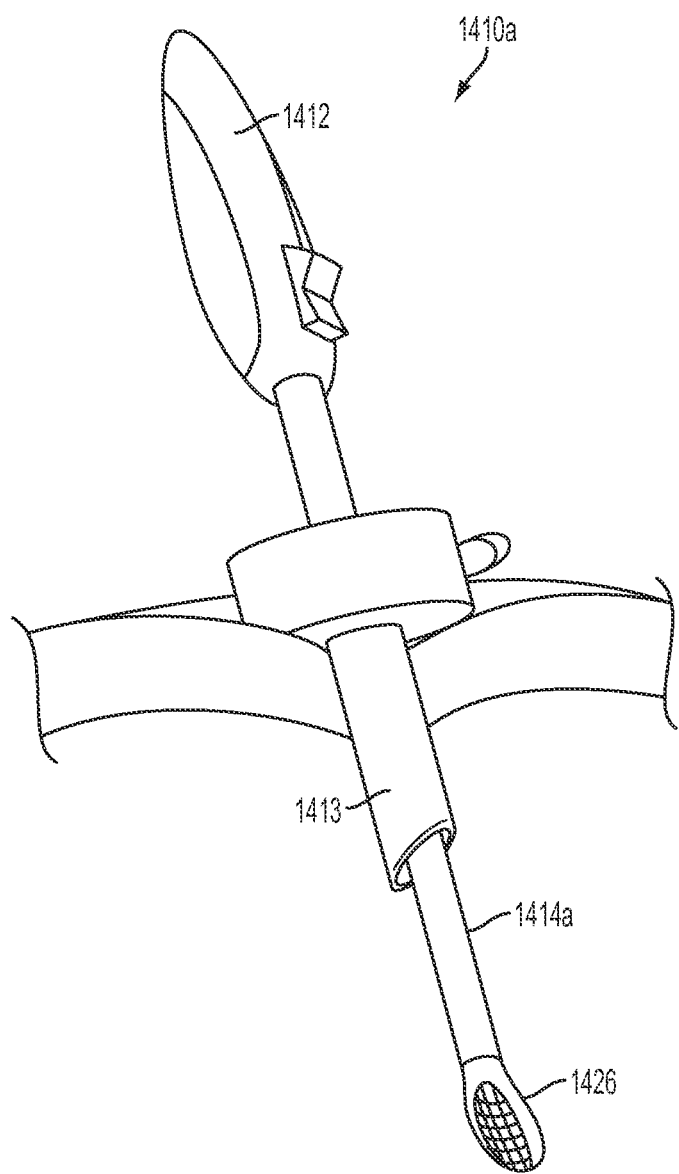

FIG. 23B illustrates one embodiment of a cordless electrosurgical instrument comprising a pencil grip handle and a laparoscopic shaft.

Figure 24A:
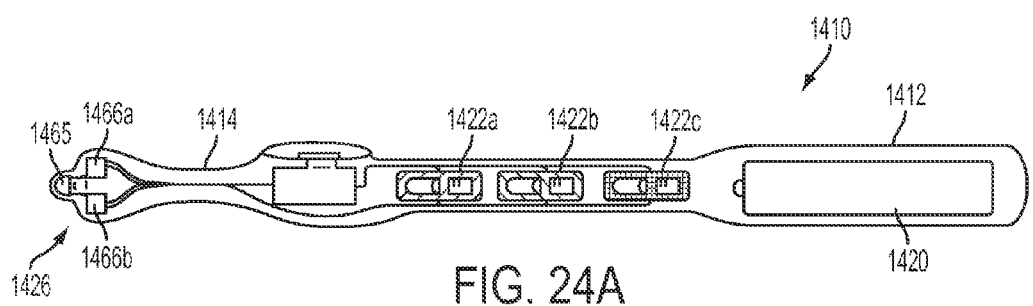

FIG. 24A illustrates on embodiment of a side view of the electrosurgical instrument of FIG. 23 with a half of a handle body removed to illustrate some of the components therein.

Figure 24B:
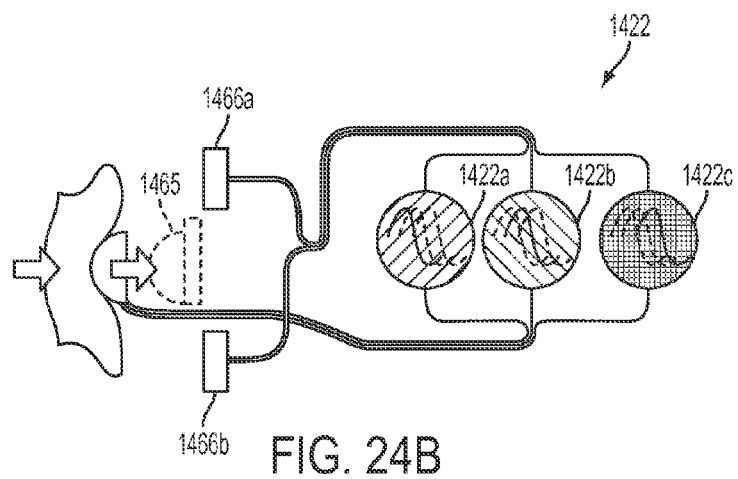

FIG. 24B illustrates one embodiment of a multi-phase signal generation element.

Figure 25A:
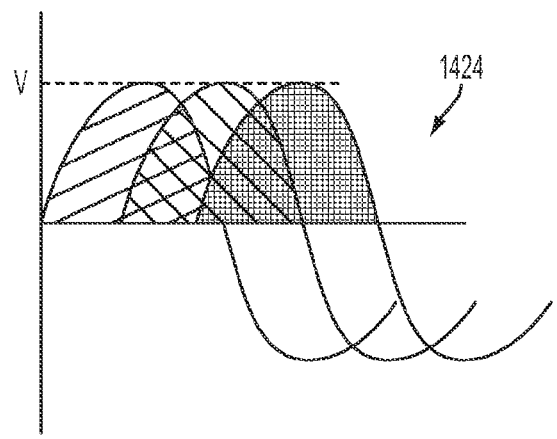

FIG. 25A illustrates an energy density curve of a three-phase multi-phase electrosurgical signal.

Figure 25B:
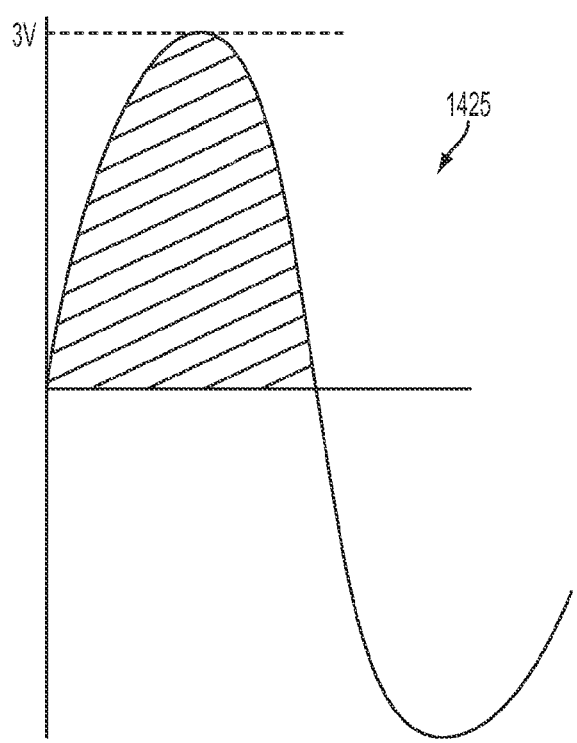

FIG. 25B illustrates an energy density of a single-phase electrosurgical signal.

Figure 26:
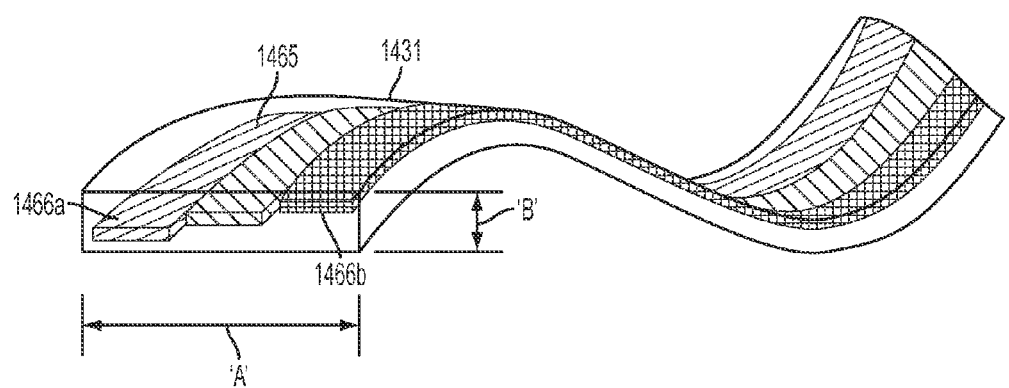

FIG. 26 illustrates one embodiment of a flat flex circuit conductor configured to transmit a multi-phase electrosurgical signal.

FIGS. 27A and 27B illustrate one embodiment of a bipolar end effector configured to deliver bipolar RF energy to a tissue section.

Figure 28C:
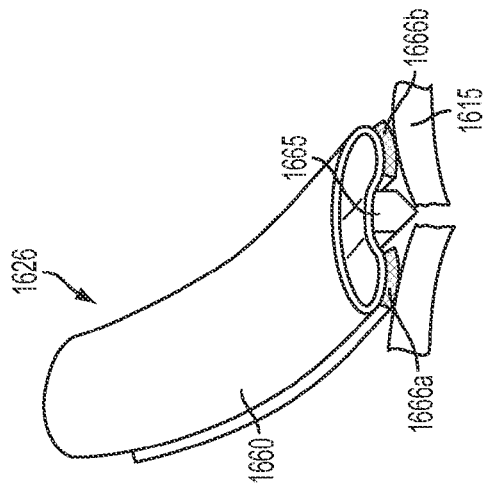
Figure 28B:
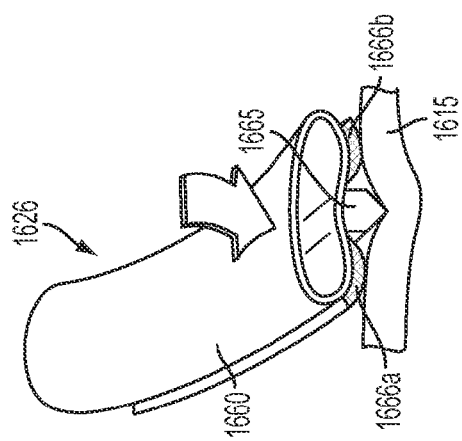
Figure 28A:
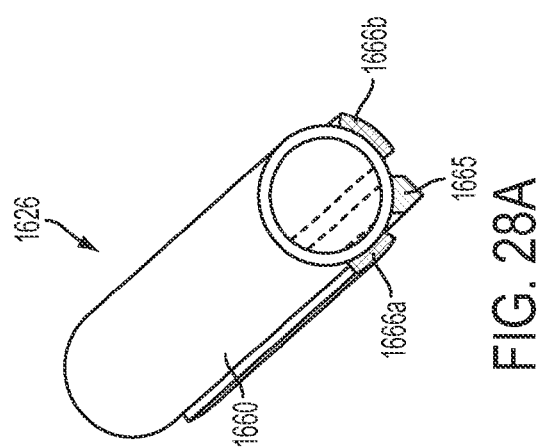

FIGS. 28A-28C illustrate one embodiment of a bipolar end effector configured to deliver bipolar RF energy to a tissue section and comprising a deformable tube.

Figure 29:
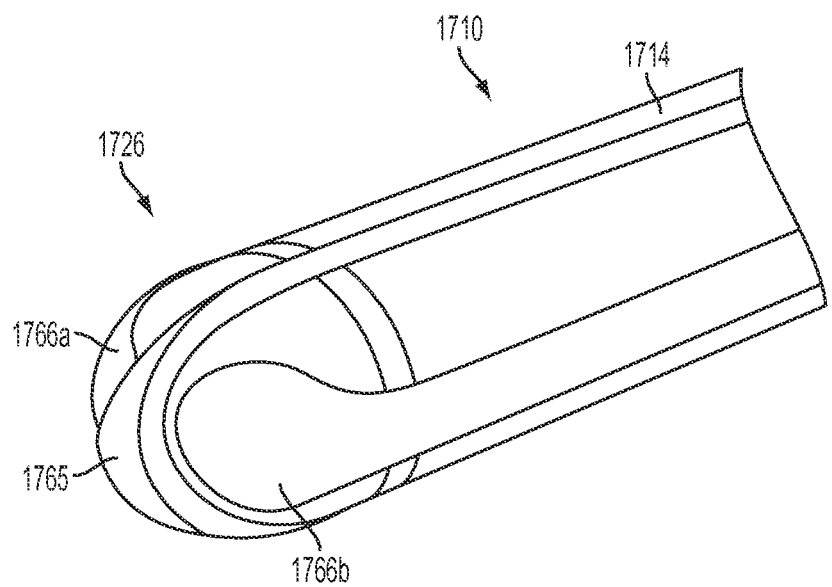

FIG. 29 illustrates one embodiment of a deformable cautery pencil tip end effector.

FIGS. 30A-30E illustrate various embodiments of deformable cautery pencil tip end effectors similar to the deformable cautery pencil tip end effector of FIG. 30.

Figure 31A:
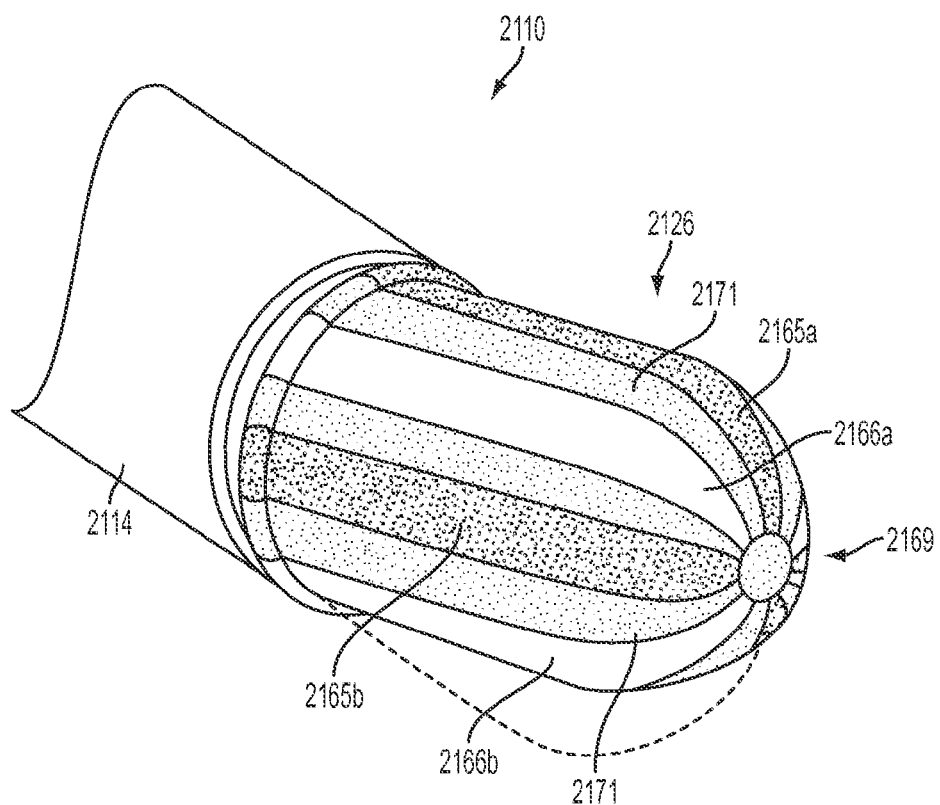
Figure 31B:
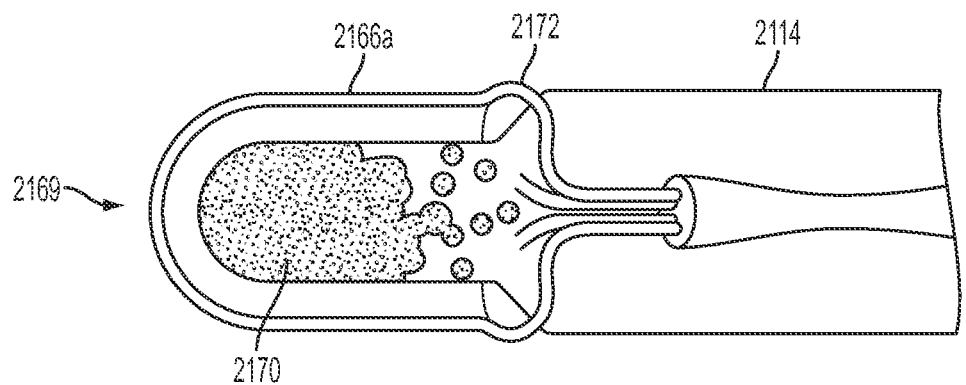
Figure 31C:
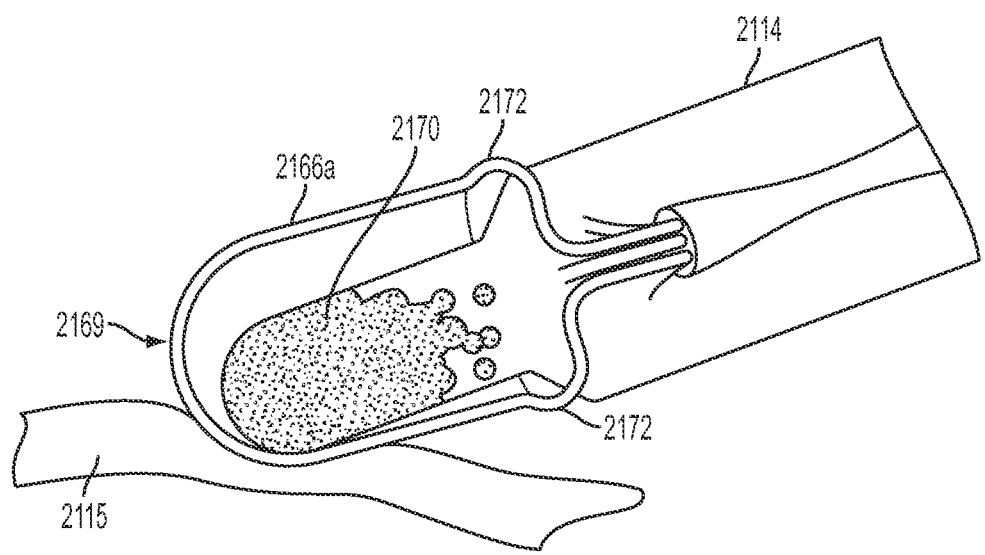

FIGS. 31A-31C illustrate on embodiment of a pencil-style electrosurgical instrument comprising a multiple electrode pencil tip end effector.

Figure 32:
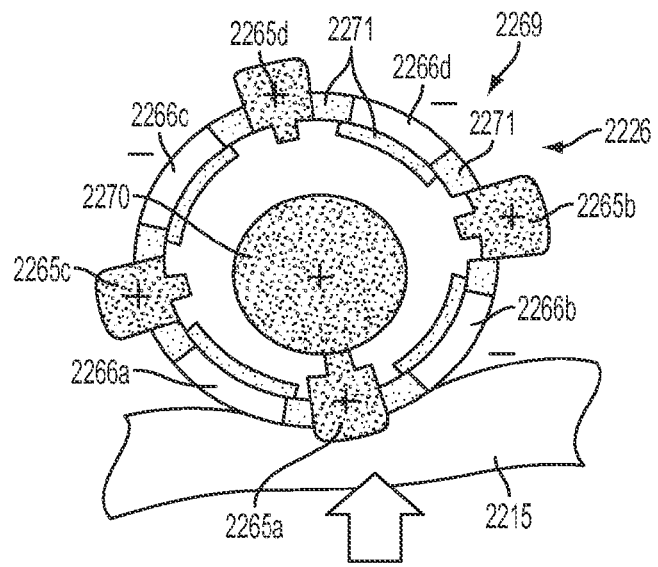

FIG. 32 illustrates one embodiment of a multiple-electrode pencil tip end effector comprising flexible plate source electrodes.

Figure 33A:
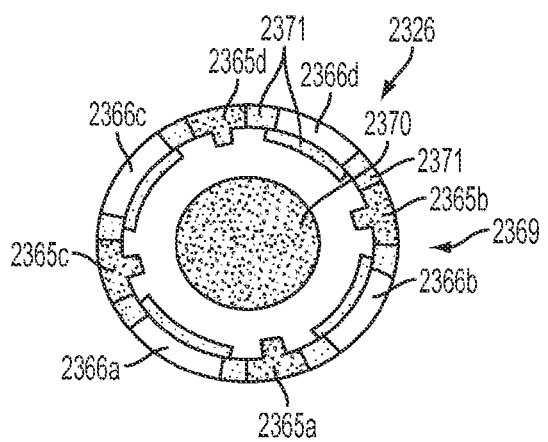
Figure 33B:
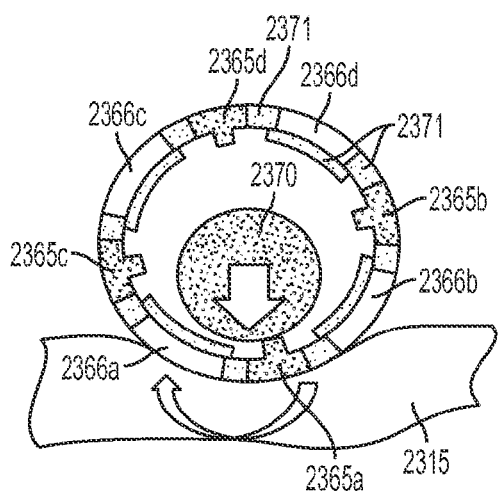

FIGS. 33A and 33B illustrates one embodiment of a multiple-electrode pencil tip end effector comprising a plurality of internal projections configured to prevent contact between an internal source electrode and a plurality of return electrodes.

Figure 34:
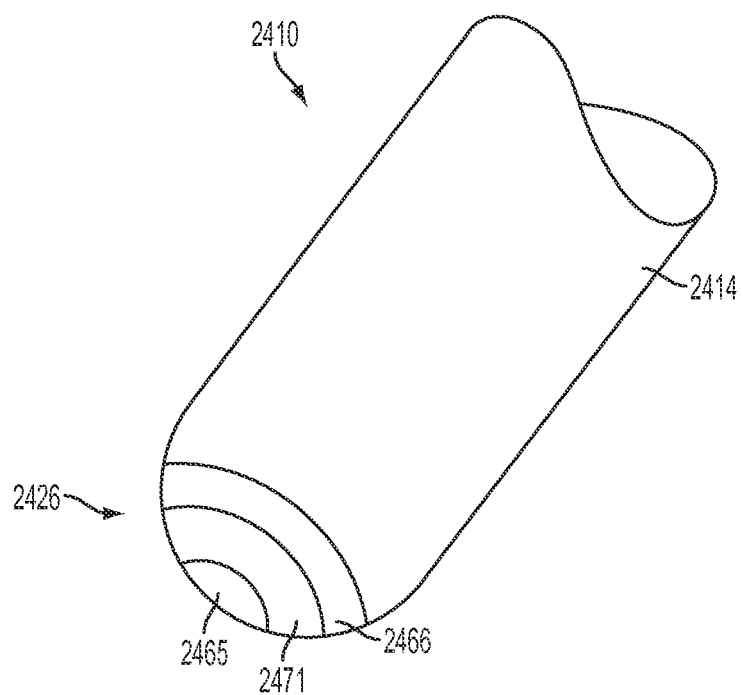

FIG. 34 illustrates one embodiment of a bipolar pencil tip end effector comprising a PTC electrode and a return electrode.

Figure 35:
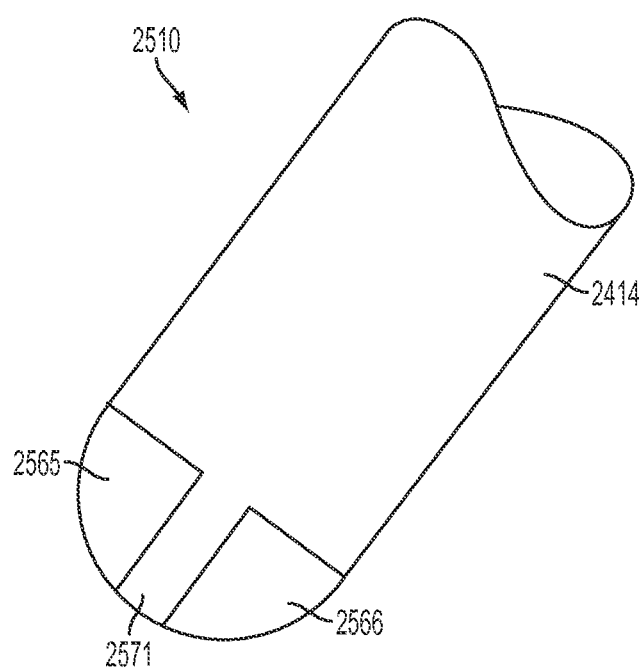

FIG. 35 illustrates one embodiment of a bipolar pencil tip end effector comprising a PTC electrode and a return electrode comprising hemispheres on a tip of the end effector.

Figure 36A:
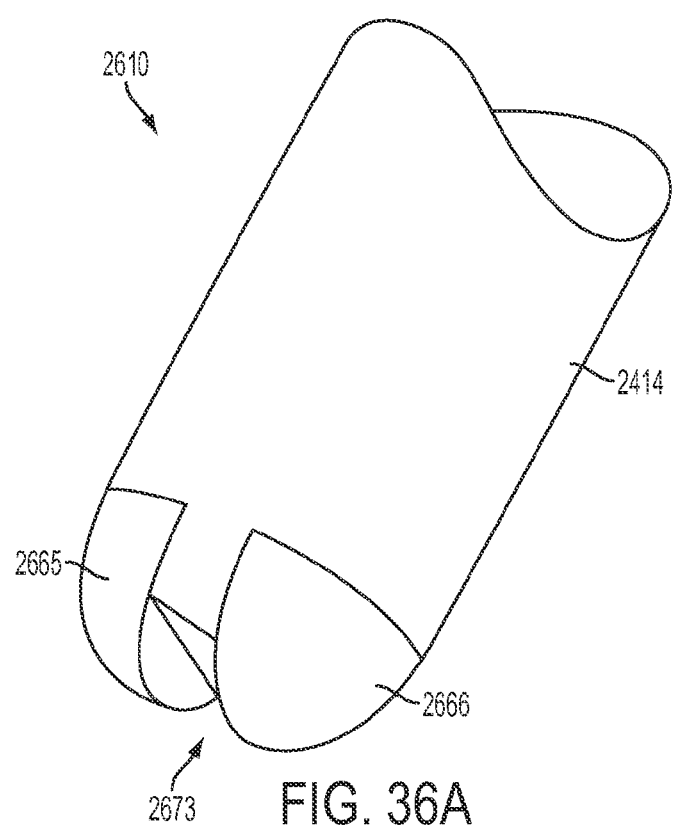
Figure 36B:
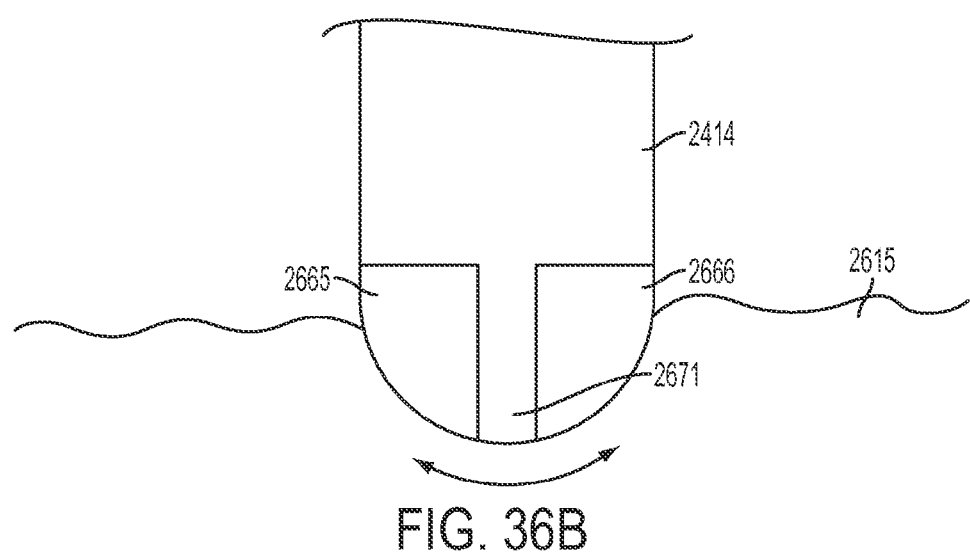

FIGS. 36A and 36B illustrate one embodiment of a bipolar pencil tip end effector comprising a PTC electrode and a return electrode comprising hemispheres on a tip of the end effector and comprising a tissue gap between the PTC electrode and the return electrode.

DESCRIPTION

Reference will now be made in detail to several embodiments, including embodiments showing example implementations of electrosurgical medical instruments for cutting and coagulating tissue. Wherever practicable similar or like reference numbers may be used in the figures and may indicate similar or like functionality. The figures depict example embodiments of the disclosed surgical instruments and/or methods of use for purposes of illustration only. One skilled in the art will readily recognize from the following description that alternative example embodiments of the structures and methods illustrated herein may be employed without departing from the principles described herein.

Various embodiments of surgical instruments that utilize therapeutic and/or subtherapeutic electrical energy to treat tissue or provide feedback to the generators (e.g., electrosurgical instruments). The embodiments are adapted for use in a manual or hand-operated manner, although electrosurgical instruments may be utilized in robotic applications as well. FIG. 1 is a perspective view of one example embodiment of a surgical instrument system 100 comprising an electrical energy surgical instrument 110. The electrosurgical instrument 110 may comprise a proximal handle 112, a distal working end or end effector 126 and an introducer or elongated shaft 114 disposed in-between.

The electrosurgical system 100 can be configured to supply energy, such as electrical energy, ultrasonic energy, heat energy, or any combination thereof, to the tissue of a patient either independently or simultaneously, for example. In one example embodiment, the electrosurgical system 100 includes a generator 120 in electrical communication with the electrosurgical instrument 110. The generator 120 is connected to the electrosurgical instrument 110 via a suitable transmission medium such as a cable 122. In one example embodiment, the generator 120 is coupled to a controller, such as a control unit 125, for example. In various embodiments, the control unit 125 may be formed integrally with the generator 120 or may be provided as a separate circuit module or device electrically coupled to the generator 120 (shown in phantom to illustrate this option). Although in the presently disclosed embodiment, the generator 120 is shown separate from the electrosurgical instrument 110, in one example embodiment, the generator 120 (and/or the control unit 125) may be formed integrally with the electrosurgical instrument 110 to form a unitary electrosurgical system 100, where a battery located within the electrosurgical instrument 110 is the energy source and a circuit coupled to the battery produces the suitable electrical energy, ultrasonic energy, or heat energy. One such example is described herein below in connection with FIGS. 7-8C.

The generator 120 may comprise an input device 135 located on a front panel of the generator 120 console. The input device 135 may comprise any suitable device that generates signals suitable for programming the operation of the generator 120, such as a keyboard, or input port, for example. In one example embodiment, various electrodes in the first jaw 164a and the second jaw 164b may be coupled to the generator 120. The cable 122 may comprise multiple electrical conductors for the application of electrical energy to positive (+) and negative (−) electrodes of the electrosurgical instrument 110. The control unit 125 may be used to activate the generator 120, which may serve as an electrical source. In various embodiments, the generator 120 may comprise an RF source, an ultrasonic source, a direct current source, and/or any other suitable type of electrical energy source, for example, which may be activated independently or simultaneously.

In various embodiments, the electrosurgical system 100 may comprise at least one supply conductor 131 and at least one return conductor 133, wherein current can be supplied to the electrosurgical instrument 100 via the supply conductor 131 and wherein the current can flow back to the generator 120 via the return conductor 133. In various embodiments, the supply conductor 131 and the return conductor 133 may comprise insulated wires and/or any other suitable type of conductor. In certain embodiments, as described below, the supply conductor 131 and the return conductor 133 may be contained within and/or may comprise the cable 122 extending between, or at least partially between, the generator 120 and the end effector 126 of the electrosurgical instrument 110. In any event, the generator 120 can be configured to apply a sufficient voltage differential between the supply conductor 131 and the return conductor 133 such that sufficient current can be supplied to the end effector 126.

Figure 2:
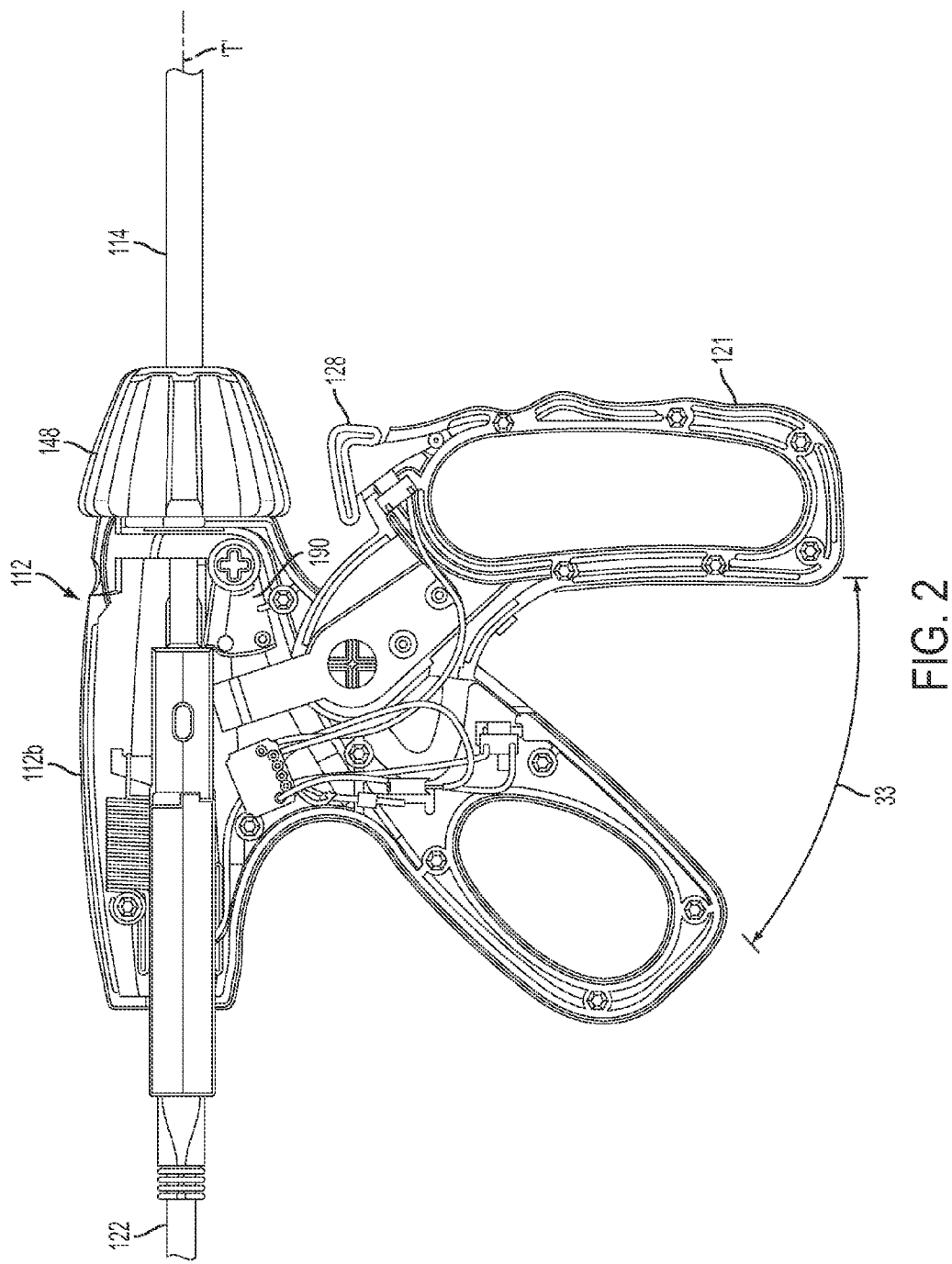
FIG. 2 illustrates a side-view of a handle of one embodiment of the surgical instrument of FIG. 1 with a half of a handle body removed to illustrates some of the components therein.

FIG. 2 is a side view of one example embodiment of the handle 112 of the surgical instrument 110. In FIG. 2, the handle 112 is shown with half of a first handle body 112a (see FIG. 1) removed to illustrate various components within the second handle body 112b. The handle 112 may comprise a lever arm 121 (e.g., a trigger) which may be pulled along a path 33. The lever arm 121 may be coupled to an axially moveable member 178 (FIGS. 3-6) disposed within the elongated shaft 114 by a shuttle 184 operably engaged to an extension 198 of lever arm 121. The shuttle 184 may further be connected to a biasing device, such as a spring 188, which may also be connected to the second handle body 112b, to bias the shuttle 184 and thus the axially moveable member 178 in a proximal direction, thereby urging the jaws 164a and 164b to an open position as seen in FIG. 1. Also, referring to FIGS. 1-2, a locking member 190 (see FIG. 2) may be moved by a locking switch 128 (see FIG. 1) between a locked position, where the shuttle 184 is substantially prevented from moving distally as illustrated, and an unlocked position, where the shuttle 184 may be allowed to freely move in the distal direction, toward the elongated shaft 114. The handle 112 can be any type of pistol-grip or other type of handle known in the art that is configured to carry actuator levers, triggers or sliders for actuating the first jaw 164a and the second jaw 164b. In some embodiments, the handle 112 may comprise a pencil-style handle. The elongated shaft 114 may have a cylindrical or rectangular cross-section, for example, and can comprise a thin-wall tubular sleeve that extends from handle 112. The elongated shaft 114 may include a bore extending therethrough for carrying actuator mechanisms, for example, the axially moveable member 178, for actuating the jaws and for carrying electrical leads for delivery of electrical energy to electrosurgical components of the end effector 126.

The end effector 126 may be adapted for capturing and transecting tissue and for contemporaneously welding the captured tissue with controlled application of energy (e.g., RF energy). The first jaw 164a and the second jaw 164b may close to thereby capture or engage tissue about a longitudinal axis "T" defined by the axially moveable member 178. The first jaw 164a and second jaw 164b may also apply compression to the tissue. In some embodiments, the elongated shaft 114, along with the first jaw 164a and second jaw 164b, can be rotated a full 360° degrees, as shown by the arrow 196 (see FIG. 1), relative to the handle 112. For example, a rotation knob 148 may be rotatable about the longitudinal axis of the shaft 114 and may be coupled to the shaft 114 such that rotation of the knob 148 causes corresponding rotation of the shaft 114. The first jaw 164a and the second jaw 164b can remain openable and/or closeable while rotated.

Figure 3:
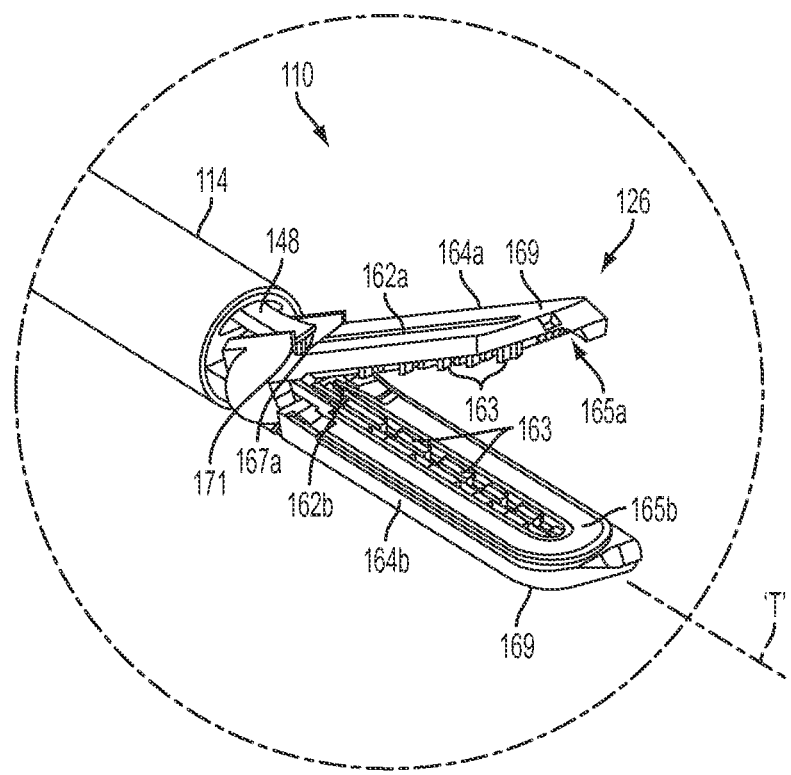
FIG. 3 illustrates a perspective view of one embodiment of the end effector of the surgical instrument of FIG. 1 with the jaws open and the distal end of an axially movable member in a retracted position.
Figure 4:
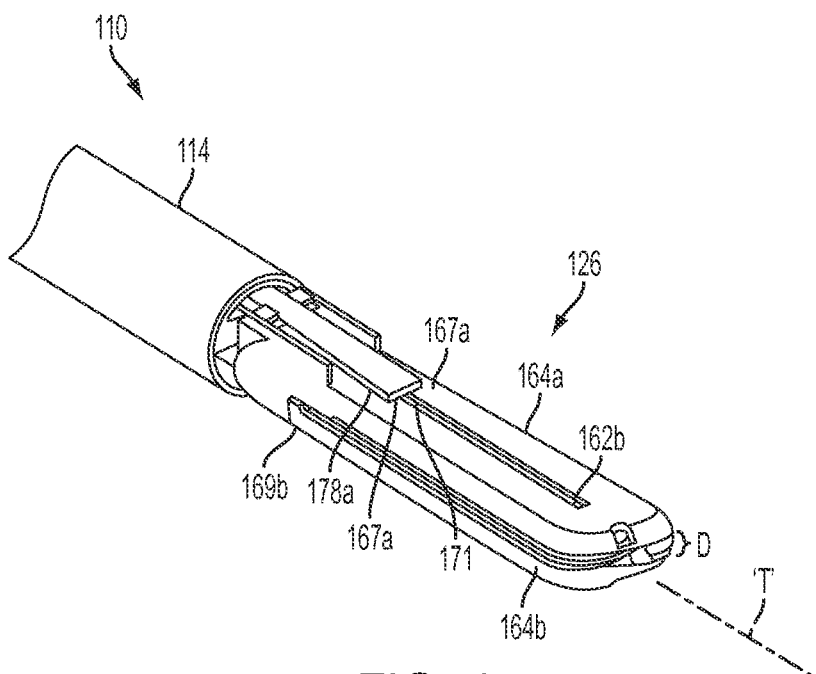
FIG. 4 illustrates a perspective view of one embodiment of the end effector of the surgical instrument of FIG. 1 with the jaws closed and the distal end of an axially moveable member in a partially advanced position.

FIG. 3 shows a perspective view of one example embodiment of the end effector 126 with the jaws 164a, 164b open, while FIG. 4 shows a perspective view of one embodiment of the end effector 126 with the jaws 164a, 164b closed. As noted above, the end effector 126 may comprise the upper first jaw 164a and the lower second jaw 164b, which may be straight or curved. The first jaw 164a and the second jaw 164b may each comprise an elongated slot or channel 162a and 162b, respectively, disposed outwardly along their respective middle portions. Further, the first jaw 164a and the second jaw 164b may each have tissue-gripping elements, such as teeth 163, disposed on the inner portions of the first jaw 164a and the second jaw 164b. The first jaw 164a may comprise an upper first jaw body 162a with an upper first outward-facing surface and an upper first energy delivery surface 165a. The second jaw 164b may comprise a lower second jaw body 162b with a lower second outward-facing surface and a lower second energy delivery surface 165b. The first energy delivery surface 165a and the second energy delivery surface 165b may both extend in a "U" shape about the distal end of the end effector 126.

Figure 5:
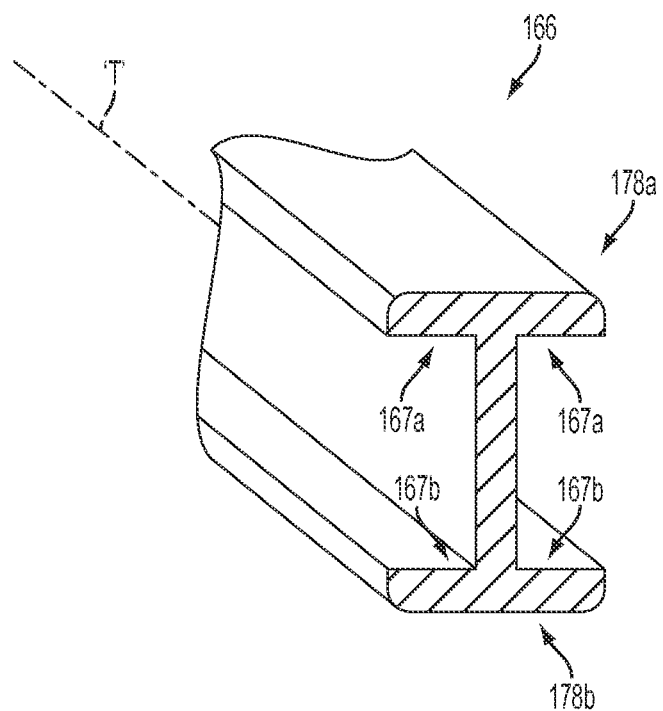
FIG. 5 illustrates a perspective view of one embodiment of the axially moveable member of the surgical instrument of FIG. 1.

The lever arm 121 of the handle 112 (FIG. 2) may be adapted to actuate the axially moveable member 178, which also may function as a jaw-closing mechanism. For example, the axially moveable member 178 may be urged distally as the lever arm 121 is pulled proximally along the path 33 via the shuttle 184, as shown in FIG. 2 and discussed above. FIG. 5 is a perspective view of one example embodiment of the axially moveable member 178 of the surgical instrument 110. The axially moveable member 178 may comprise one or several pieces, but in any event, may be movable or translatable with respect to the elongated shaft 114 and/or the jaws 164a, 164b. Also, in at least one example embodiment, the axially moveable member 178 may be made of 17-4 precipitation hardened stainless steel. The distal end of axially moveable member 178 may comprise a flanged "I"-beam configured to slide within the channels 162a and 162b in jaws 164a and 164b. The axially moveable member 178 may slide within the channels 162a, 162b to open and close the first jaw 164a and the second jaw 164b. The distal end of the axially moveable member 178 may also comprise an upper flange or "c"-shaped portion 178a and a lower flange or "c"-shaped portion 178b. The flanges 178a, 178b respectively define inner cam surfaces 167a and 167b for engaging outward facing surfaces of the first jaw 164a and the second jaw 164b. The opening-closing of jaws 164a and 164b can apply very high compressive forces on tissue using cam mechanisms which may include movable "I-beam" axially moveable member 178 and the outward facing surfaces 169a, 169b of jaws 164a, 164b.

More specifically, referring now to FIGS. 3-5, collectively, the inner cam surfaces 167a and 167b of the distal end of axially moveable member 178 may be adapted to slidably engage the first outward-facing surface 369a and the second outward-facing surface 169b of the first jaw 164a and the second jaw 164b, respectively. The channel 162a within first jaw 164a and the channel 162b within the second jaw 164b may be sized and configured to accommodate the movement of the axially moveable member 178, which may comprise a tissue-cutting element 171, for example, comprising a sharp distal edge. FIG. 4, for example, shows the distal end of the axially moveable member 178 advanced at least partially through channels 162a and 162b (FIG. 3). The advancement of the axially moveable member 178 may close the end effector 126 from the open configuration shown in FIG. 3. In the closed position shown by FIG. 4, the upper first jaw 164a and the lower second jaw 164b define a gap or dimension D between the first energy delivery surface 165a and second energy delivery surface 165b of the first jaw 164a and the second jaw 164b, respectively. In various embodiments, dimension the D can equal from about 0.0005" to about 0.040", for example, and in some embodiments, between about 0.001" to about 0.010", for example. Also, the edges of the first energy delivery surface 165a and the second energy delivery surface 165b may be rounded to prevent the dissection of tissue.

Figure 6:
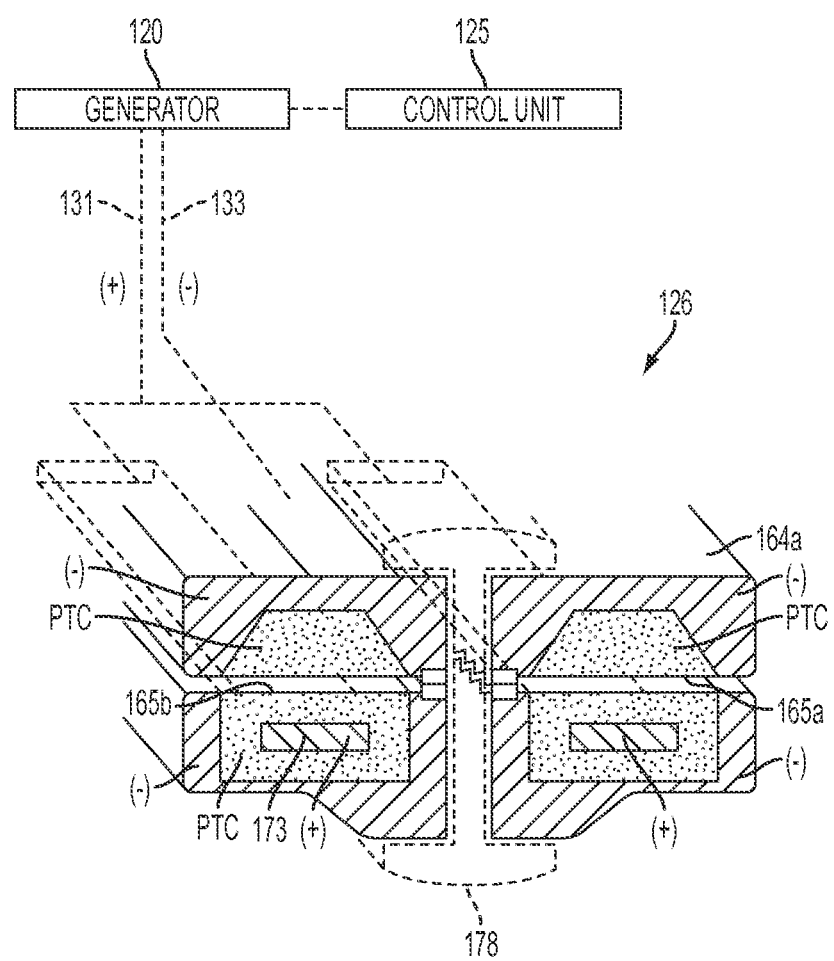
FIG. 6 illustrates a section view of one embodiment of the end effector of the surgical instrument of FIG. 1.

FIG. 6 is a section view of one example embodiment of the end effector 126 of the surgical instrument 110. The engagement, tissue-contacting, surface 165b of the lower jaw 164b is adapted to deliver energy to tissue, at least in part, through a conductive-resistive matrix, such as a variable resistive PTC body, as discussed in more detail below. At least one of the upper and lower jaws 164a, 164b may carry at least one electrode 173 configured to deliver the energy from the generator 120 to the captured tissue. The engagement, tissue-contacting, surface 165a of the upper jaw 164a may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 165a and the second energy delivery surface 165b each may be in electrical communication with the generator 120. The first energy delivery surface 165a and the second energy delivery surface 165b may be configured to contact tissue and deliver electrosurgical energy to captured tissue which are adapted to seal or weld the tissue. The control unit 125 regulates the electrical energy delivered by electrical generator 120 which in turn delivers electrosurgical energy to the first energy delivery surface 165a and the second energy delivery surface 165b. The energy delivery may be initiated by an activation button 128 (FIG. 2) operably engaged with the lever arm 121 and in electrical communication with the generator 120 via a cable 122. In one example embodiment, the electrosurgical instrument 110 may be energized by the generator 120 by way of a foot switch 129 (FIG. 1). When actuated, the foot switch 129 triggers the generator 120 to deliver electrical energy to the end effector 126, for example. The control unit 125 may regulate the power generated by the generator 120 during activation. Although the foot switch 129 may be suitable in many circumstances, other suitable types of switches can be used, such as, for example, a thumb switch.

As mentioned above, the electrosurgical energy delivered by electrical generator 120 and regulated, or otherwise controlled, by the control unit 125 may comprise radio frequency (RF) energy, or other suitable forms of electrical energy. Further, the opposing first and second energy delivery surfaces 165a and 165b may carry variable resistive PTC bodies that are in electrical communication with the generator 120 and the control unit 125. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,112; and U.S. Pat. App. Pub. Nos. 2010/0036370 and 2009/0076506, all of which are incorporated herein by reference in their entirety and made part of this specification.

In one example embodiment, the generator 120 may be implemented as an electrosurgery unit (ESU) capable of supplying power sufficient to perform bipolar electrosurgery using radio frequency (RF) energy. In one example embodiment, the ESU can be a bipolar ERBE ICC 150 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the PTC bodies and to the return electrode through the tissue. Thus, in various embodiments, the electrosurgical system 100 may comprise a supply path and a return path, wherein the captured tissue being treated completes, or closes, the circuit. In one example embodiment, the generator 120 may be a monopolar RF ESU and the electrosurgical instrument 110 may comprise a monopolar end effector 126 in which one or more active electrodes are integrated. For such a system, the generator 120 may require a return pad in intimate contact with the patient at a location remote from the operative site and/or other suitable return path. The return pad may be connected via a cable to the generator 120. In other embodiments, the operator may provide subtherapeutic RF energy levels for purposes of evaluating tissue conditions and providing feedback in the electrosurgical system 100. Such feed back may be employed to control the therapeutic RF energy output of the electrosurgical instrument 110.

During operation of electrosurgical instrument 100, the user generally grasps tissue, supplies energy to the grasped tissue to form a weld or a seal (e.g., by actuating button 128 and/or pedal 129), and then drives a tissue-cutting element 171 at the distal end of the axially moveable member 178 through the grasped tissue. According to various embodiments, the translation of the axial movement of the axially moveable member 178 may be paced, or otherwise controlled, to aid in driving the axially moveable member 178 at a suitable rate of travel. By controlling the rate of the travel, the likelihood that the captured tissue has been properly and functionally sealed prior to transection with the cutting element 171 is increased.

FIG. 7 is a perspective view of one example embodiment of a surgical instrument system 200 comprising a cordless electrical energy surgical instrument 210. The electrosurgical system 200 is similar to the electrosurgical system 100. The electrosurgical system 200 can be configured to supply energy, such as electrical energy, ultrasonic energy, heat energy, or any combination thereof, to the tissue of a patient either independently or simultaneously as described in connection with FIG. 1, for example. The electrosurgical instrument 210 may utilize the end effector 126 and elongated shaft 114 described here in conjunction with a cordless proximal handle 212. In one example embodiment, the handle 212 includes a generator circuit 220 (see FIG. 8A). The generator circuit 220 performs a function substantially similar to that of generator 120. In one example embodiment, the generator circuit 220 is coupled to a controller, such as a control circuit. In the illustrated embodiment, the control circuit is integrated into the generator circuit 220. In other embodiments, the control circuit may be separate from the generator circuit 220.

In one example embodiment, various electrodes in the end effector 126 (including the first and second jaws 164a, 164b thereof) may be coupled to the generator circuit 220. The control circuit may be used to activate the generator 220, which may serve as an electrical source. In various embodiments, the generator 220 may comprise an RF source, an ultrasonic source, a direct current source, and/or any other suitable type of electrical energy source, for example. In one example embodiment, a button 128 may be provided to activate the generator circuit 220 to provide energy to the end effector 126.

Figure 8A:
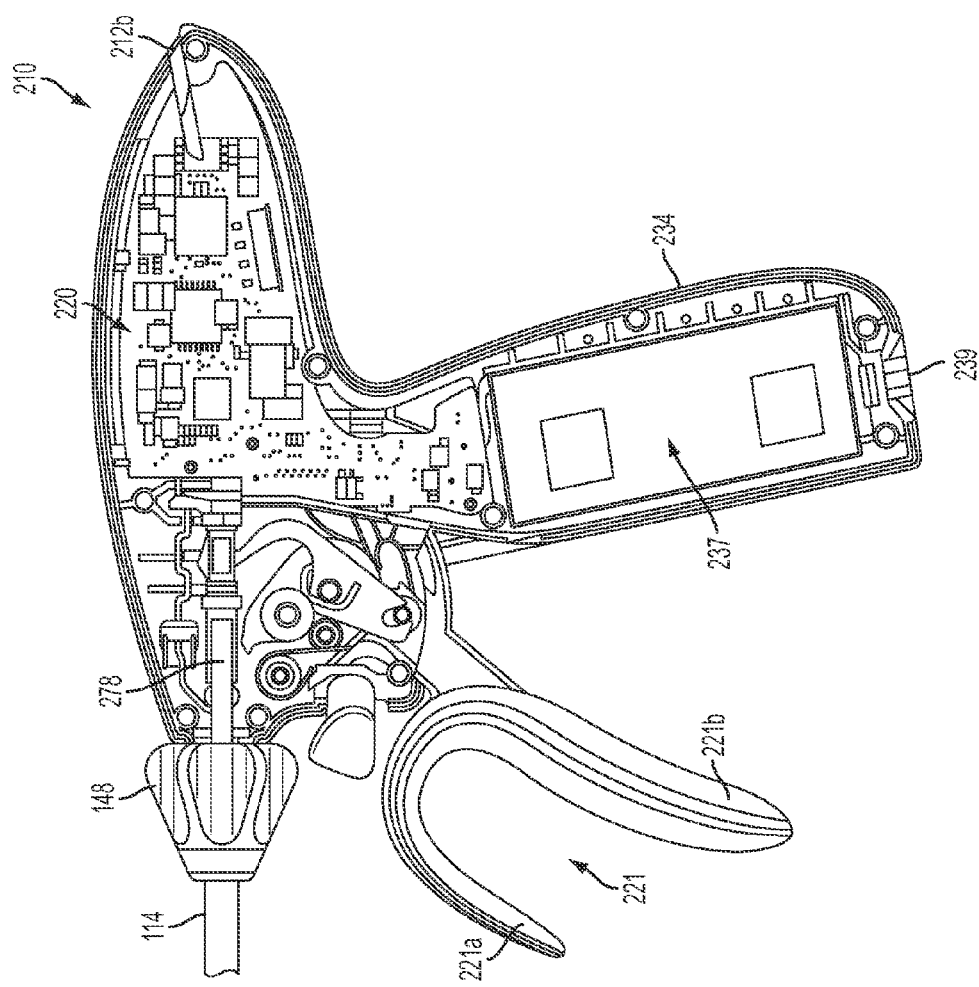
FIG. 8A illustrates a side view of a handle of one embodiment of the surgical instrument of FIG. 7 with half of the handle body removed to illustrate various components therein.

FIG. 8A is a side view of one example embodiment of the handle 212 of the cordless surgical instrument 210. In FIG. 8A, the handle 212 is shown with half of a first handle body removed to illustrate various components within the second handle body 234. The handle 212 may comprise a lever arm 224 (e.g., a trigger) which may be pulled along a path 33 around a pivot point. The lever arm 224 may be coupled to an axially moveable member 278 disposed within the elongated shaft 114 by a shuttle operably engaged to an extension of lever arm 221. In one example embodiment, the lever arm 221 defines a shepherd's hook shape comprising a distal trigger hook 221a and a proximal trigger portion 221b. As illustrated, the distal trigger hook 221a may have a first length while the proximal trigger portion 221b may have a second length with the second length greater than the first length.

In one example embodiment, the cordless electrosurgical instrument comprises a battery 237. The battery 237 provides electrical energy to the generator circuit 220. The battery 237 may be any battery suitable for driving the generator circuit 220 at the desired energy levels. In one example embodiment, the battery 237 is a 1030 mAhr, triple-cell Lithium Ion Polymer battery. The battery may be fully charged prior to use in a surgical procedure, and may hold a voltage of about 12.6V. The battery 237 may have two fuses fitted to the cordless electrosurgical instrument 210, arranged in line with each battery terminal. In one example embodiment, a charging port 239 is provided to connect the battery 237 to a DC current source (not shown).

Figure 8B:
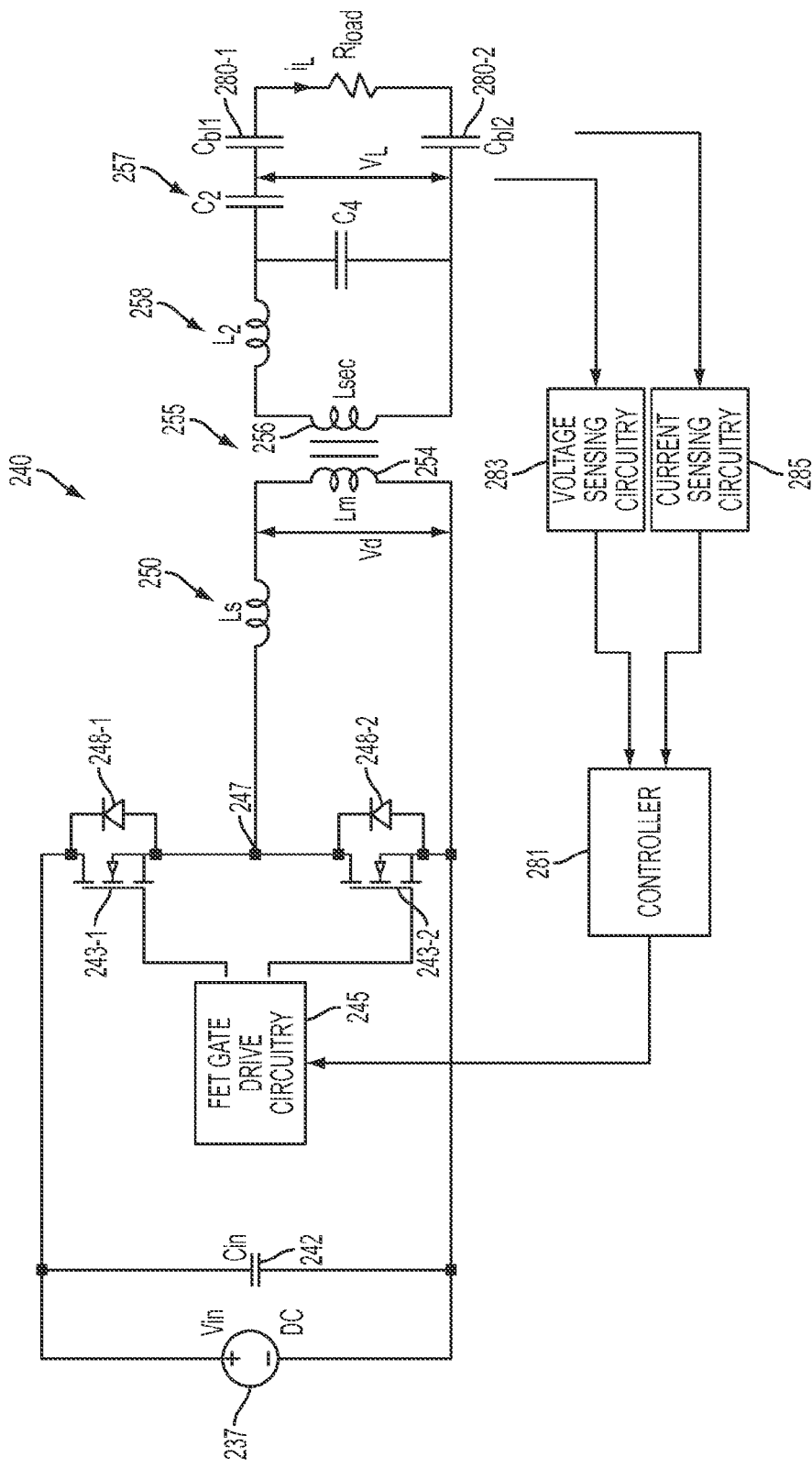
FIG. 8B illustrates one embodiment of an RF drive and control circuit.

The generator circuit 220 may be configured in any suitable manner. In some embodiments, the generator circuit comprises an RF drive and control circuit 240 and a controller circuit 282. FIG. 8B illustrates an RF drive and control circuit 240, according to one embodiment. FIG. 8B is a part schematic part block diagram illustrating the RF drive and control circuitry 240 used in this embodiment to generate and control the RF electrical energy supplied to the end effector 126. As will be explained in more detail below, in this embodiment, the drive circuitry 240 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 126. The way that this is achieved will become apparent from the following description.

As shown in FIG. 8B, the RF drive and control circuit 240 comprises the above described battery 237 are arranged to supply, in this example, about 0V and about 12V rails. An input capacitor ($C_{in}$) 242 is connected between the 0V and the 12V for providing a low source impedance. A pair of FET switches 243-1 and 243-2 (both of which are N-channel in this embodiment to reduce power losses) is connected in series between the 0V rail and the 12V rail. FET gate drive circuitry 245 is provided that generates two drive signals— one for driving each of the two FETs 243. The FET gate drive circuitry 245 generates drive signals that causes the upper FET (243-1) to be on when the lower FET (243-2) is off and vice versa. This causes the node 247 to be alternately connected to the 12V rail (when the FET 243-1 is switched on) and the 0V rail (when the FET 243-2 is switched on). FIG. 8B also shows the internal parasitic diodes 248-1 and 248-2 of the corresponding FETs 243, which conduct during any periods that the FETs 243 are open.

As shown in FIG. 8B, the node 247 is connected to an inductor-inductor resonant circuit 250 formed by inductor $L_s$ 252 and inductor $L_m$ 254. The FET gate driving circuitry 245 is arranged to generate drive signals at a drive frequency ($f_d$) that opens and crosses the FET switches 243 at the resonant frequency of the parallel resonant circuit 250. As a result of the resonant characteristic of the resonant circuit 250, the square wave voltage at node 247 will cause a substantially sinusoidal current at the drive frequency ($f_d$) to flow within the resonant circuit 250. As illustrated in FIG. 8B, the inductor $L_m$ 254 is the primary of a transformer 255, the secondary of which is formed by inductor $L_{sec}$ 256. The inductor $L_{sec}$ 256 of the transformer 255 secondary is connected to an inductor-capacitor-capacitor parallel resonant circuit 257 formed by inductor $L_2$ 258, capacitor $C_4$ 260, and capacitor $C_2$ 262. The transformer 255 up-converts the drive voltage ($V_d$) across the inductor $L_m$ 254 to the voltage that is applied to the output parallel resonant circuit 257. The load voltage ($V_L$) is output by the parallel resonant circuit 257 and is applied to the load (represented by the load resistance $R_{load}$ 259 in FIG. 8B) corresponding to the impedance of the forceps' jaws and any tissue or vessel gripped by the end effector 126. As shown in FIG. 8B, a pair of DC blocking capacitors $C_{bl}$ 280-1 and 280-2 is provided to prevent any DC signal being applied to the load 259.

In one embodiment, the transformer 255 may be implemented with a Core Diameter (mm), Wire Diameter (mm), and Gap between secondary windings in accordance with the following specifications:

Core Diameter, D (mm)
$D=19.9\times10-3$
Wire diameter, W (mm) for 22 AWG wire
$W=7.366\times10-4$
Gap between secondary windings, in gap=0.125
$G=gap/25.4$ In this embodiment, the amount of electrical power supplied to the end effector 126 is controlled by varying the frequency of the switching signals used to switch the FETs 243. This works because the resonant circuit 250 acts as a frequency dependent (loss less) attenuator. The closer the drive signal is to the resonant frequency of the resonant circuit 250, the less the drive signal is attenuated. Similarly, as the frequency of the drive signal is moved away from the resonant frequency of the circuit 250, the more the drive signal is attenuated and so the power supplied to the load reduces. In this embodiment, the frequency of the switching signals generated by the FET gate drive circuitry 245 is controlled by a controller 281 based on a desired power to be delivered to the load 259 and measurements of the load voltage ($V_L$) and of the load current ($I_L$) obtained by conventional voltage sensing circuitry 283 and current sensing circuitry 285. The way that the controller 281 operates will be described in more detail below.

In one embodiment, the voltage sensing circuitry 283 and the current sensing circuitry 285 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 283 and the current sensing circuitry 285. In one-embodiment, a step-down regulator (e.g., LT1502 by Linear Technologies) may be employed by the power save circuit to reduce the supply voltage of the rail-to-rail amplifiers and thus extend the life of the battery 237.

Figure 8C:
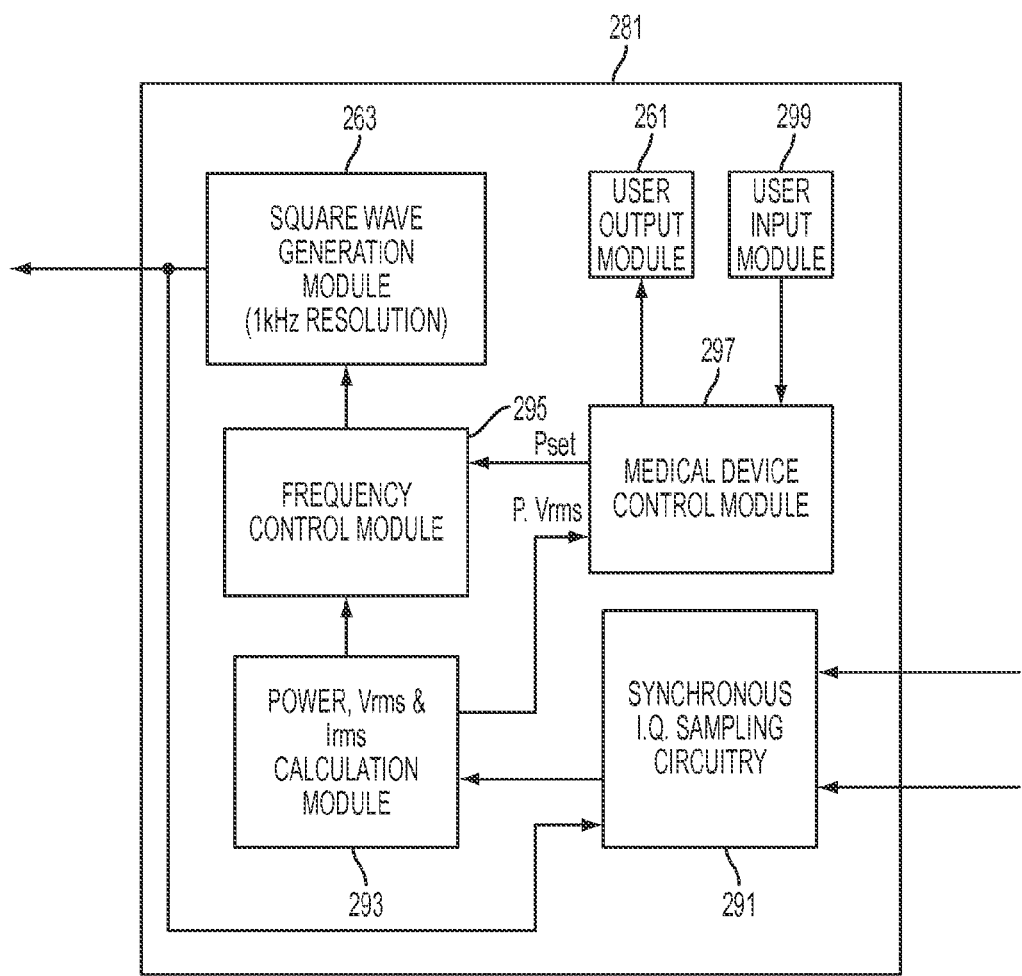
FIG. 8C illustrates one embodiment of the main components of a control circuit.

FIG. 8C illustrates the main components of the controller 281, according to one embodiment. In the embodiment illustrated in FIG. 8C, the controller 281 is a microprocessor based controller and so most of the components illustrated in FIG. 8c are software based components. Nevertheless, a hardware based controller 281 may be used instead. As shown, the controller 281 includes synchronous I,Q sampling circuitry 291 that receives the sensed voltage and current signals from the sensing circuitry 283 and 285 and obtains corresponding samples which are passed to a power, $V_{rms}$ and $I_{rms}$ calculation module 293. The calculation module 293 uses the received samples to calculate the RMS voltage and RMS current applied to the load 259 (FIG. 8B; end effector 126 and tissue/vessel gripped thereby) and from them the power that is presently being supplied to the load 259. The determined values are then passed to a frequency control module 295 and a medical device control module 297. The medical device control module 297 uses the values to determine the present impedance of the load 259 and based on this determined impedance and a pre-defined algorithm, determines what set point power ($P_{set}$) should be applied to the frequency control module 295. The medical device control module 297 is in turn controlled by signals received from a user input module 299 that receives inputs from the user (for example pressing buttons or activating the control levers 114, 110 on the handle 104) and also controls output devices (lights, a display, speaker or the like) on the handle 104 via a user output module 261.

The frequency control module 295 uses the values obtained from the calculation module 293 and the power set point ($P_{set}$) obtained from the medical device control module 297 and predefined system limits (to be explained below), to determine whether or not to increase or decrease the applied frequency. The result of this decision is then passed to a square wave generation module 263 which, in this embodiment, increments or decrements the frequency of a square wave signal that it generates by 1 kHz, depending on the received decision. As those skilled in the art will appreciate, in an alternative embodiment, the frequency control module 295 may determine not only whether to increase or decrease the frequency, but also the amount of frequency change required. In this case, the square wave generation module 263 would generate the corresponding square wave signal with the desired frequency shift. In this embodiment, the square wave signal generated by the square wave generation module 263 is output to the FET gate drive circuitry 245, which amplifies the signal and then applies it to the FET 243-1. The FET gate drive circuitry 245 also inverts the signal applied to the FET 243-1 and applies the inverted signal to the FET 243-2.

The electrosurgical instrument 210 may comprise additional features as discussed with respect to the electrosurgical system 100 illustrated in FIGS. 1-6. Those skilled in the art will recognize that electrosurgical instrument 210 may include a rotation knob 148, an elongated shaft 114, and an end effector 126. These elements function in a substantially similar manner to that discussed above with respect to the electrosurgical system 100 illustrated in FIGS. 1-6. In one example embodiment, the cordless electrosurgical instrument 210 may include visual indicators 235. The visual indicators 235 may provide a visual indication signal to an operator. In one example embodiment, the visual indication signal may alert an operator that the device is on, or that the device is applying energy to the end effector. Those skilled in the art will recognize that the visual indicators 235 may be configured to provide information on multiple states of the device.

In some embodiments, one or more of the components of the upper and lower jaws 164a, 164b may comprise a fluoropolymer material comprising an electrically conductive mica additive. For example, in one embodiment, the tissue contact surfaces 165a, 165b of the upper and lower jaws 164a, 164b may comprise the fluoropolymer material. In some embodiments, the fluoropolymer material may comprise polytetrafluoroethylene (PTFE). PTFE comprises a non-stick, non-electrically conductive material. Electrically conductive mica comprises mica coated with a conductive material, such as, for example, nickel or silver. The electrically conductive mica additive may allow the PTFE material to transmit an electrosurgical signal from a conductor to a tissue section.

In some embodiments, a fluoropolymer material comprising an electrically conductive mica additive may be added to one or more components of the upper and lower jaws 164a, 164b as a compression molded structural component adhered to and/or overmolded to a substrate such as, for example, stainless steel. In one embodiment, the fluoropolymer material may be applied as a spray to a supporting metal structure, such as, for example, stainless steel. The fluoropolymer material may comprise a thickness of, for example, 5-20 microns. In some embodiments the fluoropolymer material may comprise a mica content of 0.1-10% by weight.

Figure 9:
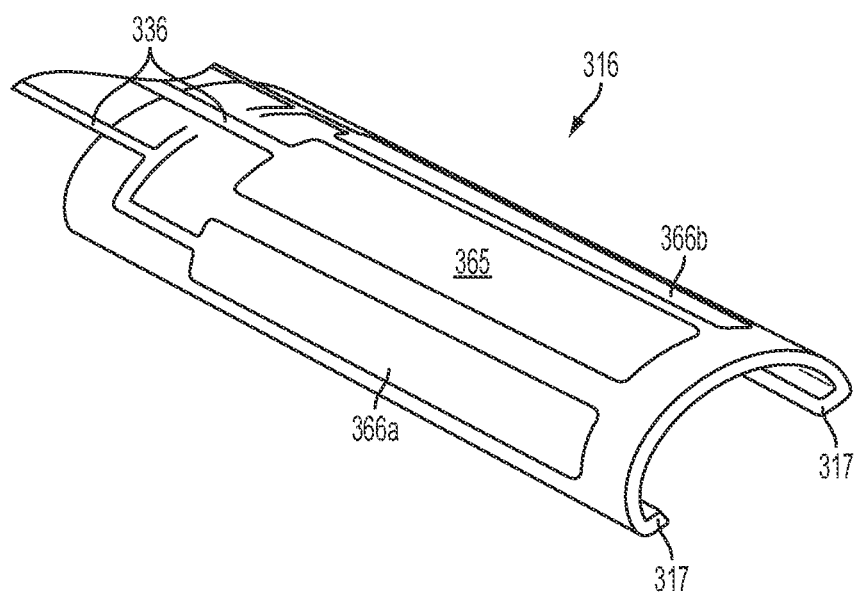
FIG. 9 illustrates one embodiment of a molded base cap configured to interface with the bottom jaw of the end effector of the surgical instrument in FIGS. 1 and 7.

FIG. 9 illustrates one embodiment of a one-piece flexible snap-on base cap 316. The base cap 316 may be configured to interface with the end effector 126, for example, by snapping or clipping onto the lower jaw 164b. The base cap 316 may comprise at least one source electrode 365 and one or more return electrodes 366a, 366b. The source electrode 365 and the return electrodes 366a, 366b may be coupled to a generator, for example the generator 120 shown in FIG. 1, when the base cap 316 is coupled to an end effector 126. The base cap 316 may comprise one or more flex circuits 336 configured to couple the electrodes 365, 366a, 366b to, for example, the conductors 131, 133 located within the shaft 114 of the electrosurgical device 110.

In some embodiments, the base cap 316 may comprise one or more molded hook caps 317 for mounting the base cap 316 to a lower jaw 164b. The molded hook caps 317 may be bonded into the base cap 316, for example, as part of an electrode layer. The molded hook caps 317 may be configured to interface with one or more features of the lower jaw 164b to mount the base cap 316 onto the lower jaw 164b.

Figure 10A:
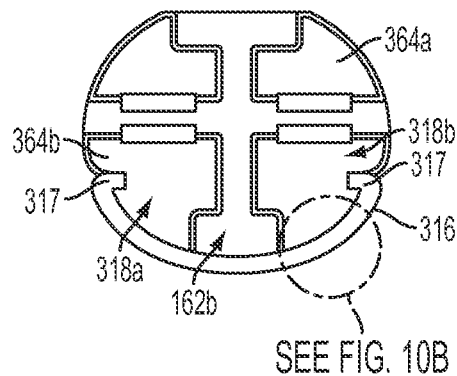
FIGS. 10A and 10B illustrate one embodiment of a molded base cap interfaced with the bottom jaw of an electrosurgical end effector, where
Figure 10B:
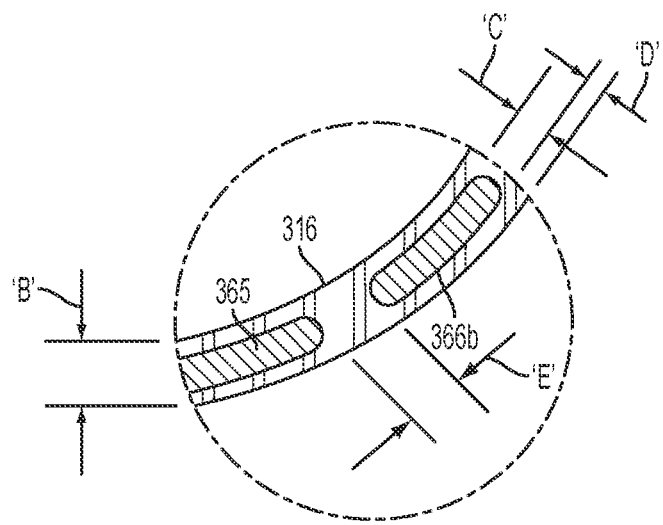

FIGS. 10A and 10B illustrate one embodiment of the base cap 316 coupled to an end effector 326, where FIG. 10B is a detailed view of a section of the molded base cap shown in FIG. 10A. The base cap 316 may comprise one or more features, such as, for example, the molded hook caps 317, configured to interface with one or more features of the end effector 326. The end effector 326 may comprise one or more overhangs 318a, 318b configured to interface with the molded hook caps 317 formed on the base cap 316. In some embodiments, the base cap 316 may be configured to cover an I-Beam channel 162b in a lower jaw 164b of the electrosurgical device 110. FIG. 10B illustrates a detailed cross-sectional view of the base cap 316. In one embodiment, the base cap 316 may comprise a width 'B' of approximately 0.01"-0.02". The electrodes 365, 366a, 366b may comprise, for example, a printed circuit comprising a width 'C' of approximately 0.005" with a clearance 'D' of approximately 0.002" on either side of the electrodes 365, 366a, 366b. The electrodes 365, 366a, 366b may comprise a spacing 'E', for example, of approximately 0.006"-0.008" within the base cap 316.

As shown in FIG. 10B, the base cap 316 may comprise a source electrode 365 and one or more return electrodes 366a, 366b. The source electrode 365 and the return electrodes 366a, 366b may comprise a flexible, printed circuit. The electrodes 365, 366a, 366b may be coupled to a source conductor 131 and a return conductor 133 of the electrosurgical device 110 through flex circuit 336. In operation, the base cap 316 may be used for bipolar coagulation and/or cautery of a tissue section in contact with the base cap 316. The base cap 316 may allow treatment of a tissue section located between the return electrodes 366a, 366b while protecting the electrosurgical instrument 310, such as, for example, the I-Beam channel 162b, from debris and fouling during application of electrosurgical energy.

Figure 11:
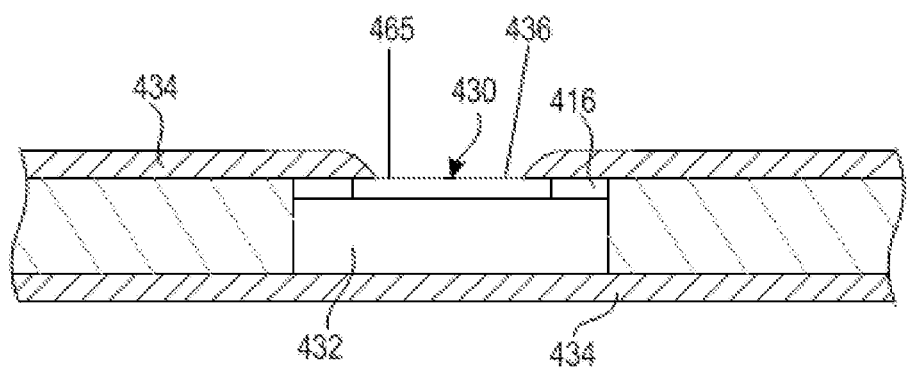
FIG. 11 illustrates one embodiment of the base cap of FIG. 9 comprising an electrode layer, a heat sink layer, and a sealing layer applied in a laminate structure.

In some embodiments, the base cap 316 may comprise one or more laminate layers. FIG. 11 illustrates one embodiment of a base cap 416 comprising an electrode layer 430, a heat sink layer 432, and a sealing layer 434 applied in a laminate structure. The sealing layer 434 may comprise a flex circuit formed thereon. The flex circuit may be configured to provide a connection with the supply conductor 1 and the return conductor from the generator, for example, the generator 120 shown in FIG. 1. In the illustrated embodiment, the electrode layer 430 may comprise a direct contact metal electrode 465 configured for direct application of electrosurgical energy to a tissue section. In some embodiments, the electrode layer 430 may comprise an inductive coupling electrode (not shown). A direct contact electrode embodiment may require less voltage to weld tissue but may be affected by becoming dirty or fouled over time. In some embodiments, a biocompatible dielectric grease or coating may be included on the direct contact metal electrode 465 to minimize degradation in performance. In some embodiments, an isolative material may be deposited between the electrodes 465 in the electrode layer 430. For example, in one embodiment, an isolative plastic 436 may be bonded onto base cap 416 around the printed electrodes 465.

The base cap 416 may comprise an insulative layer 432 configured to isolate the electrodes from the lower jaw 164b of the electrosurgical instrument 110. A middle electrode layer 430 may comprise a plurality of printed electrodes 465. The printed electrodes 465 may comprise flexible circuits. An outer sealing layer 434 may be disposed over the insulative layer 432 and the electrode layer 430 to seal the base cap. The sealing layer 434 may comprise any suitable material, such as, for example, polyethylene, polypropylene, and/or nylon. The sealing layer 434 may comprise any suitable thickness, such as, for example, 1 to 2 mils. In some embodiments, the inner layer may comprise a thickness of between 0.01" to 0.015" with each of the electrodes comprising a thickness of about 0.005". In some embodiments, the electrodes may comprise a specific spacing on the base cap, such as, for example, a spacing of 0.06" to 0.08".

Figure 12:
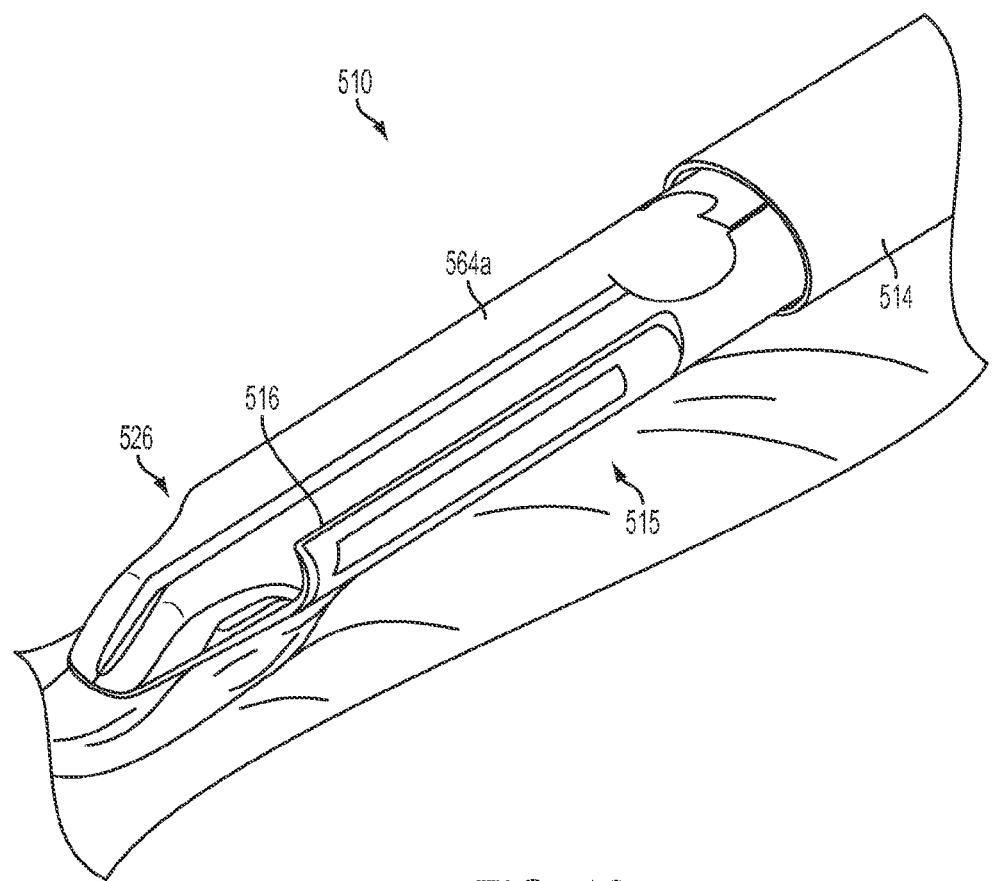
FIG. 12 illustrates one embodiment of the base cap of FIG. 9 in contact with and energizing a tissue section.

FIG. 12 illustrates one embodiment of an electrosurgical instrument 510 comprising an end effector 526. A base cap 516 is coupled to the end effector 526. The base cap 516 may be configured to provide electrosurgical energy to a tissue section 515. An operator may apply a force to the tissue section 515 using the base cap 516. The base cap 516 may apply an electrosurgical signal to the tissue section 515. The base cap 516 may be used, for example, to provide touch-up electrosurgical treatment after a cutting and sealing operation performed by the end effector 526. The base cap 516 may be configured to cover an I-beam slot 162b in the lower jaw 564b to prevent debris from entering into, or damage occurring to, the I-beam slot 162b during touch-up electrosurgical treatment.

Figure 13:
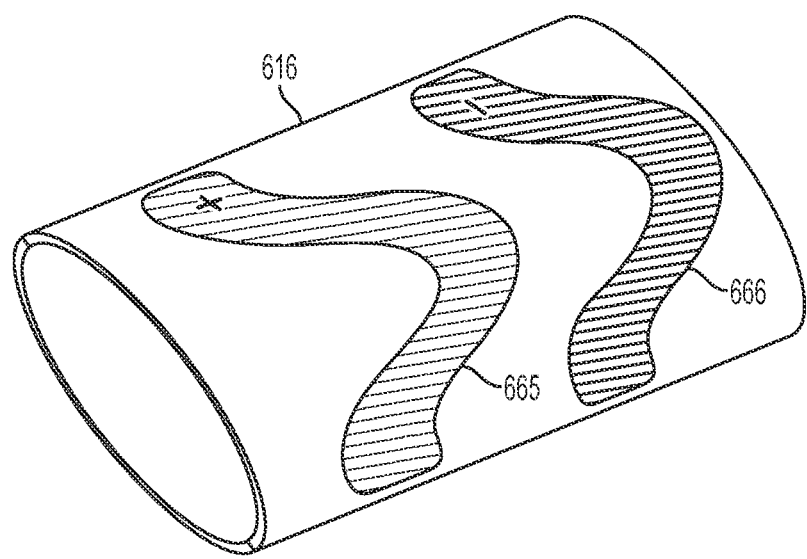
FIGS. 13-15 illustrate various electrode arrangements for various embodiments of the base cap of FIG. 9.
Figure 14:
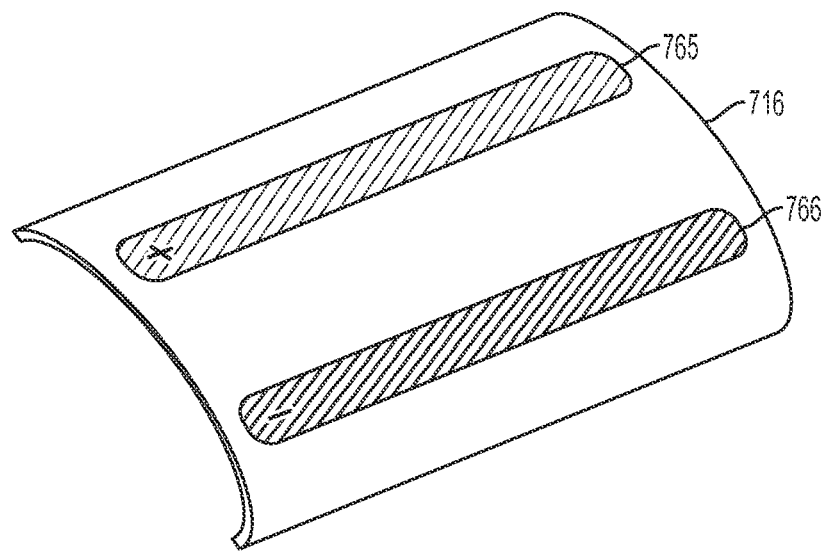
Figure 15:
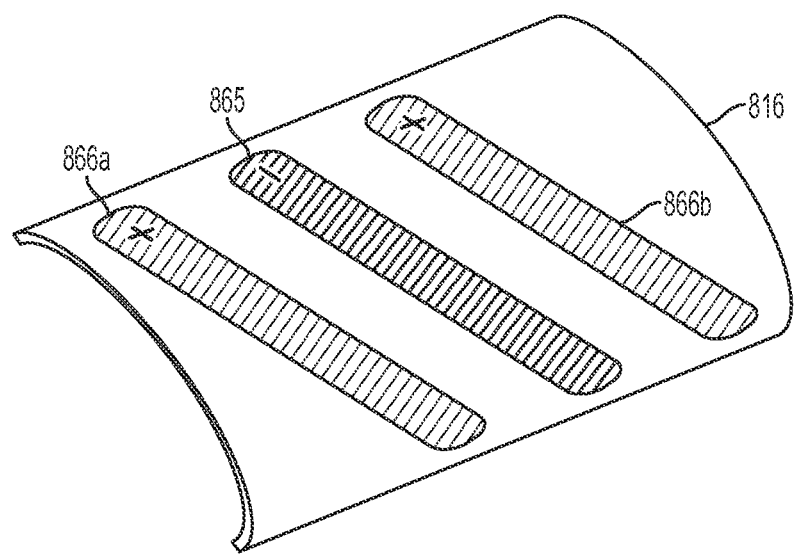

FIGS. 13-15 illustrate base caps comprising various electrode arrangements. FIG. 13 illustrates a base cap 616 comprising a first electrode 665a and a second electrode 665b. The first electrode 665a and the second electrode 665b define a treatment area therebetween. When the base cap 616 is in contact with a tissue section and an electrosurgical signal is applied to the first electrode 665a and the second electrode 665b, for example, by a generator 120, a tissue weld may occur between the first electrode 665a and the second electrode 665b. FIG. 14 illustrates one embodiment of base cap 716 comprising longitudinal first and second electrodes 765a, 765b. FIG. 15 illustrates one embodiment of base cap 816 comprising a source electrode 865 and two return electrodes 866a, 866b. The treatment area of the base cap 816 may comprise the area between the two return electrodes 866a, 866b, as current may flow from the source electrode 865 into both of the return electrodes 866a, 866b.

In some embodiments, the electrosurgical instrument 110 may comprise additional tissue treatment features. FIGS.

16A and 16B illustrate one embodiment of an electrosurgical instrument 910 comprising an end effector 926. The end effector 926 may comprise a tissue ablation tip 963. In FIG. 16A a perspective of the end effector 926 shows a jaw member in an open position and in FIG. 16B an end view of the end effector 926 shows the jaw members in a closed position. With reference now to both FIGS. 16A and 16B, a central electrode 965 may be deposited on the upper jaw 964a and the lower jaw 964b. The central electrode 965 may be separated into an upper hemisphere 967a formed on the upper jaw 964a and a lower hemisphere 967b formed on the lower jaw 964b. A return electrode 966 may be formed on the distal end of the upper jaw 964a and the lower jaw 964b. The return electrode 966 may comprise, for example, a ring electrode. The return electrode 966 may be concentric with the central electrode 965. The return electrode 966 may be separated into an upper hemisphere 968a formed on the upper jaw 964a and a lower hemisphere 968b formed on the lower jaw 964b. The central electrode 965 and the return electrode 966 may be coupled to the generator 120 through the upper jaw 964a and/or the lower jaw 964b. In some embodiments, the central electrode 965 may comprise a PTC material. As the temperature of a tissue section increases due to treatment by the electrosurgical device 910, the PTC material of the central electrode 965 may limit the current flow through the tissue section, providing temperature controlled-limits for delivered electrosurgical energy.

In some embodiments, only one hemisphere of the central electrode 965 and/or the return electrode 966 may be coupled to the generator 120. For example, in one embodiment, only the upper hemispheres of the central electrode 967a and/or the return electrode 968a may be coupled to the generator 120. In this embodiment, when the upper jaw 964a and the lower jaw 964b are in an open position, only the upper hemispheres 967a, 968a of the central electrode 965 and the return electrode 966 may be active. When the upper jaw 964a and the lower jaw 964b are in a closed position, current may flow to the lower hemispheres 967b, 968b from the upper hemispheres 967a, 968a of the electrodes 965, 966.

The electrosurgical device 910 may comprise a closure switch configured to indicate closure of the upper jaw 964a and the lower jaw 964b and to control operation of the tissue ablation tip 963. For example, in one embodiment, a closure switch may be configured to control operation of the tissue ablation tip 963. When the upper jaw 964a and the lower jaw 964b are in an open position, the closure switch may prevent operation of the tissue ablation tip 963. When the upper jaw 964a and the lower jaw 964b are in a closed position, the closure switch may allow operation of the tissue ablation tip 963. In another embodiment, the closure switch may be configured to switch between monopolar and bipolar treatments. For example, in one embodiment, when the upper jaw 964a and the lower jaw 964b are in an open position, the closure switch may configure the upper hemisphere 967a of the central electrode 965 and/or the upper hemisphere 968a of the return electrode 966 for monopolar electrosurgical treatment. When the upper jaw 964a and the lower jaw 964b are in a closed position, the closure switch may provide bipolar electrosurgical energy to the tissue ablation tip 963.

In some embodiments, the electrosurgical instrument 110 may comprise a power tip. FIG. 17 illustrates one embodiment of an end effector 1026 comprising a power tip 1040. The power tip 1040 may comprise an electrode 1042 disposed at the distal end of the end effector 1026. The end effector 1026 may comprise an upper jaw 1064a and a lower jaw 1064b. The power tip 1040 may be disposed on the distal end of the lower jaw 1064b. The power tip 1040 may comprise a wire and/or other conductive material configured to receive monopolar and/or bipolar RF energy. The power tip 1040 may be configured to allow a surgeon to generate an otomy, or aperture, in a tissue section, by applying a force to the tissue section using the power tip 1040. Monopolar or bipolar RF energy may be applied to the power tip 1040 to cause heating of the tissue section. FIG. 18 illustrates one embodiment of a half-circle power tip 1140 disposed on the distal end of a lower jaw 1164b. The half-circle power tip 1140 may be similar to the wire power tip 1040 shown in FIG. 17.

In some embodiments, the power tip 1040 may be coupled to a generator configured to generate an ultrasonic signal and/or an RF signal, such as, for example, the generator 120 shown in FIG. 1. In one embodiment, the power tip 1040 may be configured to receive the signal from an ultrasonic module and/or an electrosurgical module of the generator 120. The power tip 1040 may be configured to provide monopolar and/or bipolar energy to a tissue section. In bipolar mode, one or more electrodes in the upper jaw 1064a and/or the lower jaw 164b may function as return electrodes.

FIG. 19 illustrates one embodiment of an electrical connection between a generator 1220, a power tip 1240, a ground electrode 1266, and one or more electrodes 1265 disposed in a clamp jaw, such as, for example, the upper jaw 1064a and the lower jaw 1064b. A switch 1244, such as, for example, a two-pole switch 1344 (see FIG. 20), may be configured to control delivery of energy to the power tip 1240. For example, in a first position, the power tip 1240 may be configured to receive a signal from the electrosurgical module and/or the ultrasonic module of the generator 1220. In a second position, the power tip 1240 may be deactivated and one or more electrodes 1265 in the clamp jaw 1064a, 1064b may be configured to receive energy from the electrosurgical module of the generator 1120. FIG. 20 illustrates one embodiment of a two-pole switch 1344 configured to control the operation of a power tip 1240. The switch 1344 may be configured to alternate between monopolar and bipolar electrosurgical energy. In some embodiments, the two-pole switch 1344 may be configured to switch delivery of electrosurgical energy from one or more electrodes 1265 to a power tip 1240.

In some embodiments, a monopolar add-on device may be configured to interface with the electrosurgical instrument 110 and/or a power tip 1240. For example, as shown in FIGS. 21 and 22, an electrosurgical instrument 1310 may be configured to receive a monopolar add-on device 1350. The monopolar add-on device 1350 may comprise an annular slip ring 1352. The monopolar add-on device 1350 may be configured to slide and/or clip onto the electrosurgical device 1310, for example, over the shaft 1314. The monopolar add-on device 1350 may be located, for example, on the shaft 1314 distal of a rotator 148. The annular slip ring 1352 may be configured to interface with one or more of the conductors located in the shaft 1314. In some embodiments, the monopolar add-on may comprise a power switch 1354 and a power cord 1322 configured to interface with a monopolar generator (not shown).

In some embodiments, the monopolar add-on device 1350 may comprise a pencil grip 1356. The pencil grip 1356 may enable a surgeon to perform touch-up and/or other precise monopolar treatment without the need to switch devices. In some embodiments, the monopolar add-on device 1350 may be configured to disable bipolar operation of the electrosurgical device 1310 when the monopolar add-on device 1350 is interfaced with the electrosurgical device 1310. In some embodiments, the monopolar add-on device 1350 may be controlled by a foot controller (not shown).

In some embodiments, the monopolar add-on device 1350 may be configured to provide monopolar energy to a power tip disposed on the distal end of the electrosurgical device 1310. For example, as shown in FIG. 17, a power tip 1040 may be disposed on the distal end of an end effector 1026. The power tip 1040 may be configured to receive monopolar energy from the monopolar add-on device 1350. The power tip 1040 may be coupled to a conductor configured to interface with the slip ring 1352 of the monopolar add-on device 1350.

FIG. 23A illustrates one embodiment of an electrosurgical instrument 1410 comprising a pencil-grip handle 1412. The pencil-grip handle 1412 may provide precise control of the electrosurgical instrument 1410 for performing spot and/or small section treatment. In one embodiment, the pencil-grip handle 1412 may be coupled to a shaft 1414. The shaft 1414 may comprise various lengths such as, for example, a shorter length for open-surgery electrosurgical instruments or a longer shaft for laparoscopic/endoscopic electrosurgical instruments. The shaft 1414 may be coupled to an end effector 1426. FIG. 23B illustrates one embodiment of an electrosurgical instrument 1410a configured for laparoscopic surgical procedures. The surgical instrument 1410a is similar to the electrosurgical instrument 1410. The surgical instrument 1410a comprises the handle 1412, a laparoscopic shaft 1414a, and the end effector 1426. The surgical instrument 1410a may be inserted into a patient through, for example, a trocar 1413.

In some embodiments, the end effector 1426 may comprise one or more electrodes for providing electrosurgical instrument to a tissue section. For example in some embodiments, the end effector 1426 may be configured to provide monopolar and/or bipolar RF energy to a treatment site. The end effector 1426 may comprise one or more electrodes configured to deliver monopolar and/or bipolar energy to a tissue section. For example, in one embodiment, the end effector 1426 may comprise at least one source electrode 1465 and at least one return electrode 1466 configured to deliver bipolar RF energy to a tissue section in contact with the end effector 1426. In some embodiments, the end effector 1426 may be configured to receive ultrasonic energy.

One embodiment of a cordless cautery bipolar pencil 1410 is now disclosed with reference to FIGS. 23A and 24A. The cordless cautery bipolar pencil 1410 may utilize the shaft 1414 and/or the end effectors 1426, 1526, 1626, 1726, 1926, 2026, 2126, 2226, 2326, 2426, 2526, 2626 discussed with respect to FIGS. 23A-34. In various embodiments, the cordless cautery bipolar pencil 1410 may be configured to provide bipolar energy to a treatment area through the end effector 1426. FIG. 24A illustrates a cross-sectional view of the cordless cautery bipolar pencil 1410 shown in FIG. 23A. The cordless cautery bipolar pencil 1410 may comprise a power source 1420, such as, for example, a battery, rechargeable or non-rechargeable. The cordless cautery bipolar pencil 1410 may comprise one or more signal generation circuits 1422a, 1422b, 1422c. In some embodiments, the signal generation circuits 1422a-C may comprise a multi-phase power generation circuit 1422.

A multi-phase power generation circuit 1422 may be configured to produce multi-phase power for the bipolar end effector 1426. The multi-phase power generation circuit 1422 may provide any suitable multi-phase signal, such as, for example, a three-phase signal, to the end effector 1426. The use of a multi-phase signal may reduce the current and/or voltage requirements of the bipolar end effector 1426 while still delivering the same amount of energy density to the electrodes 1465, 1466a, 1466b. By reducing the current requirements of the end effector 1426, the impact of heat generation at the electrodes 1465, 1466a, 1466b may be reduced. For example, when a three-phase signal is used, the current/voltage requirements of the electrosurgical device 1410 may be three times less than the current/voltage requirements of a single-phase electrosurgical system. By reducing the current requirement by a factor of three, the impact of heat generation, $i^2r$, may be reduced by a factor of nine.

FIG. 24B illustrates one embodiment of a multi-phase signal generation element 1422. A plurality of single-phase signal generators 1422a-C may be configured to generate a single-phase bipolar electrosurgical signal. The plurality of single phase signals may be combined to generate the multi-phase bipolar signal. Each of the single-phase signal generators 1422a-C may be coupled to a source electrode 1465 and one or more return electrodes 1466a, 1466b. Although a three-phase multi-phase signal generator 1422 is illustrated, those skilled in the art will recognize that any number of single-phase generators 1422a-C may be combined in a multi-phase signal generator.

FIG. 25A illustrates the energy density of a three-phase multi-phase signal 1424. FIG. 25B illustrates the energy density of a single-phase electrosurgical signal 1425. As shown in FIGS. 25A and 25B, the energy density of a three-phase signal with a maximum voltage 'v' is equal to the energy density of a single-phase signal 1425 with a maximum voltage of '3 v', or three times the voltage of the multi-phase signal 1424. The use of a multi-phase signal may allow treatment of a tissue section using a lower voltage and/or lower current signal. The lower voltage and/or lower current of the multi-phase signal 1424 may allow the use of a thinner conductor than a conductor used for a single-phase signal 1425. For example, in one embodiment, a 34 gauge wire used for a single-phase signal 1425 may be replaced with three circuit paths of 0.001"×0.020" per conductor. In some embodiments, the multi-phase conductors may comprise flat conductors. For example, in one embodiment, the multi-phase circuit paths may comprise flat flex circuits. FIG. 26 illustrates one embodiment of a flat multi-phase signal conductor 1431.

A multi-phase signal, such as, for example, the multi-phase signal 1424 illustrated in FIG. 25A, may be transmitted to the end effector 1426 and the tissue section by a flat flex circuit conductor 1431. In one, non-limiting embodiment, the flat conductor 1431 may comprise a circuit path ('A'×'B') of 0.1"×0.01". The flex circuit flat conductor 1431 may facilitate connections and lamination of the circuit paths on top of one another, reducing the area needed for multiple circuit paths. In one embodiment, individual conductor circuit paths 1465, 1466a, 1466b may comprise, for example, a circuit path of 0.02"×0.001".

In one embodiment, an end effector of an electrosurgical instrument, such as, for example, electrosurgical instruments 110, 1410 shown in FIGS. 1 and 23A, may comprise one or more electrodes configured to deliver bipolar RF energy to a tissue section in contact with the end effector. FIGS. 27A and 27B illustrate one embodiment of a bipolar end effector 1526 configured to deliver bipolar RF energy to a tissue section. The bipolar end effector 1526 may comprise one or more electrodes 1565, 1566a, 1566b. The one or more electrodes 1565, 1566a, 1566b, may be deployable from the shaft 1514. For example, in one embodiment, the one or more electrodes 1565, 1566a, 1566b may be coupled to conductors 1531, 1533a, 1533b extending through the shaft 1514 to the proximal end of an electrosurgical device 1510. A surgeon may slide the conductors 1531, 1533a, 1533b distally and/or proximally to deploy or retract the one or more electrodes 1565, 1566a, 1566b from the shaft 1514. In some embodiments, the electrodes 1565, 1566a, 1566b may be coupled to an actuator (not shown) for deploying the electrodes 1565, 1566a, 1566b from the shaft 1514.

In some embodiments, the end effector 1526 may comprise at least one source electrode 1565. The source electrode 1565 may be coupled to, for example, a positive pole of a bipolar RF energy source. The end effector 1526 may comprise a plurality of return electrodes 1566a, 1566b. The plurality of return electrodes 1566a, 1566b may be coupled to, for example, a negative pole of a bipolar RF energy source. The source electrode 1565 and the plurality of return electrodes 1566a, 1566b may be deployable from the shaft 1514 to define a treatment area. In some embodiments, the plurality of return electrodes 1566a, 1566b may define a treatment area with the source electrode 1565 located substantially at the center of the treatment area. For example, as shown in FIG. 27A, the end effector 1526 comprises a first return electrode 1566a and a second return electrode 1566b. The first and second return electrodes 1566a, 1566b are located on opposite sides of the source electrode 1565. A user may deploy the electrodes 1565, 1566a, 1566b from the shaft 1514. The electrodes 1565, 1566a, 1566b may contact a tissue section 1515 and may define a treatment area in which bipolar energy may be delivered to the tissue section 1515.

In one embodiment, the plurality of return electrodes 1566a, 1566b may be biased away from the source electrode 1565. For example, in one embodiment, the first return electrode 1566a and the second return electrode 1566b may be spring-biased away from the source electrode 1565. When the biased return electrodes 1566a, 1566b are deployed from the shaft 1514, the return electrodes 1566a, 1566b may fan out to define a wider treatment area (see FIG. 27B). In some embodiments, the return electrodes 1566a, 1566b may be biased away from the tissue section 1515 and the source electrode 1565 may be biased towards the tissue section. In order to create a circuit between the source electrode 1565 and the return electrodes 1566a, 1566b, the end effector 1526 may be pressed into the tissue section 1515 until the return electrodes 1566a, 1566b are in contact with the tissue section 1515. In this embodiment, the center source electrode 1565 exerts a higher pressure on the tissue section 1515 than the outer return electrodes 1566a, 1566b. If drawn along the tissue section 1515, the high pressure center source electrode 1565 may cut the tissue section 1515 like a blade. The area between the source electrode 1565 and the return electrodes 1566a, 1566b may be simultaneously coagulated during cutting.

FIGS. 28A-28C illustrate one embodiment of a bipolar electrosurgical end effector 1626 comprising a deformable tube 1660. The deformable tube 1660 may have a plurality of electrodes 1665, 1666a, 1666b disposed on the outer surface of the deformable tube 1660. The deformable tube 1660 may provide mechanical forces similar to those discussed above with respect to FIGS. 27A and 27B. For example, in one embodiment, the end effector 1626 may comprise a deformable tube 1660 comprising a source electrode 1665, a first return electrode 1666a, and a second return electrode 1666b. The first and second return electrodes 1666a, 1666b may be disposed on opposite sides of the deformable tube 1660. In operation, a surgeon may move the end effector 1626 into contact with a tissue section. The operator may apply a force to the source electrode 1665 by applying a distal force to, for example, a pencil-grip handle (not shown). The force applied to the source electrode 1665 may cause the deformable tube 1660 to flex or deform into, for example, an oval configuration, as shown in FIG. 28B.

The first and second return electrodes 1666a, 1666b may be arranged on the outer surface of the deformable tube 1660 such that when the deformable tube 1660 is in a deformed state, such as, for example, due to a force applied by a tissue section 1615 to the source electrode 1665, the first and second return electrodes 1666a, 1666b rotate into contact with the tissue section 1615 to define a treatment area. In some embodiments, the source electrode 1665 may comprise a high pressure electrode and/or a blade. As shown in FIG. 28C, the end effector 1626 may be drawn along the tissue section 1615 to cut the tissue section 1615 at the source electrode 1665 and simultaneously coagulate the tissue section 1615 between the source electrode 1665 and each of the return electrodes 1666a, 1666b.

FIG. 29 illustrates one embodiment of a deformable cautery pencil tip end effector 1726. The deformable cautery pencil tip end effector 1726 may comprise at least one high pressure electrode 1765, a first distributed pressure electrode 1766a, and a second distributed pressure electrode 1766b. The deformable cautery pencil tip end effector 1726 may comprise a deformable section 1760. As the end effector 1726 is pressed into a tissue section by an operator, the deformable cautery pencil tip end effector 1726 may deform at the deformable section 1760 to provide contact between the first and second distributed pressure electrodes 1766a, 1766b and the tissue section. In some embodiments, the deformable cautery pencil tip end effector 1726 may comprise a circular cross-section when in a rest state and may deform into an oval cross-section when a force is applied to the high pressure electrode 1765.

In some embodiments, the high pressure electrode 1765 may comprise a rigid electrode configured to focus pressure applied by an operator into a small surface area tip. The distributed pressure electrodes 1766a, 1766b may comprise flexible electrodes comprising larger surface areas than the high pressure electrode 1765. In some embodiments, the high pressure electrode 1765 may be coupled to a positive pole of a bipolar RF generator and the distributed pressure electrodes 1766a, 1766b may be coupled to a negative pole of a bipolar RF generator, such as, for example, the generator 120 shown in FIG. 1. In some embodiments, the high pressure electrode 1765 may comprise a longitudinally rigid tip configured to provide longitudinal stiffness and strength to the deformable cautery pencil tip end effector 1626.

In some embodiments, cutting may occur at the tip of the high pressure electrode 1765 due to the high, tight energy density at the tip. Simultaneous with the cutting, coagulation may occur in a treatment area located between the high pressure electrode 1765 and the distributed pressure electrodes 1766a, 1766b. Additional coagulation may occur over the surface area of the distributed pressure electrodes 1766a, 1766b in contact with the tissue section. In some embodiments, the high pressure electrode 1765 and/or the distributed pressure electrodes 1766a, 1766b may comprise a metal material. The distributed pressure electrodes 1766a, 1766b may comprise, for example, a super-elastic metal such as, for example, nitinol.

Figure 30A:
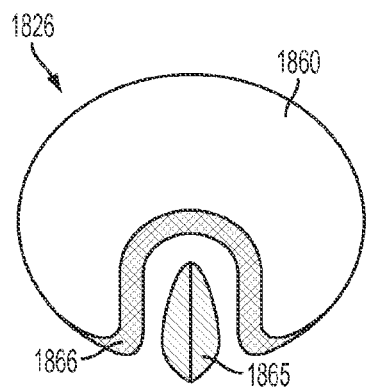
Figure 30B:
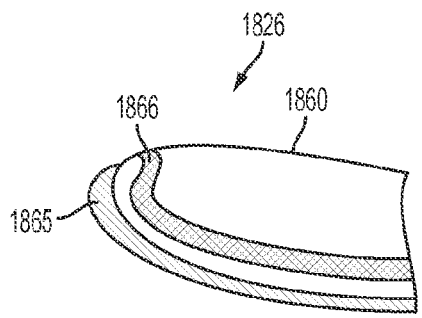
Figure 30C:
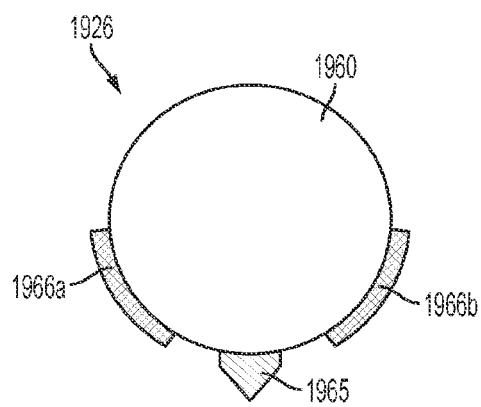
Figure 30D:
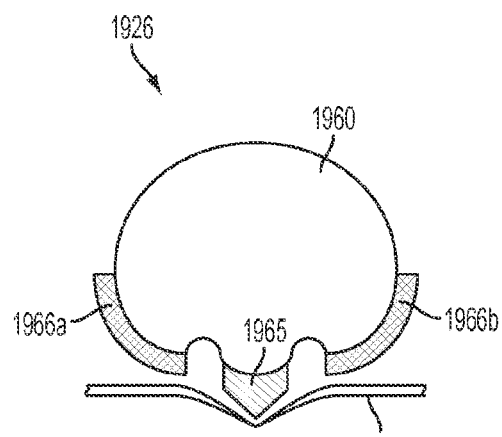

FIGS. 30A-30E illustrate various embodiments of deformable cautery pencil tip end effectors. For example, FIG. 30A illustrates a distal end of a deformable cautery pencil tip end effector 1826 comprising a longitudinal high pressure electrode 1865 and a continuous distributed pressure electrode 1866. FIG. 30B illustrates a side-view of the end effector 1826. As illustrated in FIGS. 30A and 30B, the distributed pressure electrode 1866 is disposed about the high pressure electrode 1865 to provide a contact area on both sides of the longitudinal high pressure electrode 1866. FIGS. 30C and 30D illustrate one embodiment of a single-sided bipolar bladed pencil end effector 1926. The single-sided end effector 1926 may comprise a longitudinal high pressure electrode 1965, a first distributed pressure electrode 1966*a*, and a second distributed pressure electrode 1966*b*. FIG. 30D illustrates the single-sided end effector 1926 in a deformed position when pressure is applied to a tissue section 1915 by the longitudinal high pressure electrode 1965. As shown in FIG. 30D, when a force is applied to the high pressure electrode 1965 by a tissue section 1915, the end effector 1926 deforms to allow the first and second distributed electrodes 1966*a*, 1966*b* to rotate into contact with the tissue section 1915 and provide a current path for delivering bipolar electrosurgical energy to the tissue section 1915.

Figure 30E:
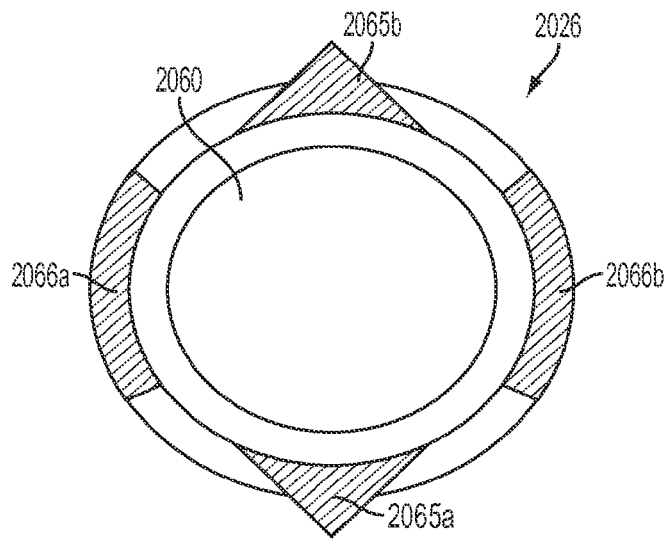

FIG. 30E illustrates one embodiment of a double-sided bipolar bladed pencil end effector 2026. The double-sided end effector 2026 may comprise a first high pressure electrode 2065*a* and a second high pressure electrode 2065*b* disposed on opposite sides of the end effector 2026. A first distributed pressure electrode 2066*a* and a second distributed pressure electrode 2066*b* may be disposed on opposite sides of the end effector 2026 between the high pressure electrodes 2065*a*, 2065*b*. The end effector 2026 may comprise a deformable section 2060 such that if a force is applied by either of the high pressure electrodes 2065*a*, 2065*b* to a tissue section, the deformable section 2060 may deform to allow the distributed pressure electrodes 2066*a*, 2066*b* to contact the tissue section and define a treatment area therebetween.

FIGS. 31A-31C illustrate one embodiment of a pencil-style electrosurgical instrument 2110 comprising a multiple-electrode pencil tip end effector 2126. The multiple-electrode pencil tip end effector 2126 may comprise a plurality of source electrodes 2165*a*-2165*b* and a plurality of return electrodes 2166*a*-2166*b*. In some embodiments, the plurality of source electrodes 2165*a*-B and the plurality of return electrodes 2166*a*-B may comprise an alternating arrangement about the perimeter of the multiple-electrode pencil tip end effector 2126. The plurality of source electrodes 2165*a*-B and the plurality of return electrodes 2166*a*-B may define a hollow-dome head 2169. The dome head 2169 may be attached to the shaft 2114.

In some embodiments, the return electrodes 2166*a*-B may be coupled to an RF generator through one or more conductors (not shown) extending through the shaft 2114. An internal source electrode 2170 may be located within the dome head 2169. The internal source electrode 2170 may be coupled to the RF generator through a conductor 2131 extending through the shaft 2114. In some embodiments, when a force is applied to the dome head 2169, such as, for example, by pushing the dome head 2169 in to a tissue section 2115, the dome head 2169 and/or the internal source electrode 2170 may flex to create a connection between the internal source electrode 2170 and at least one of the plurality of source electrodes 2165*a*-B located on the dome head 2169. The source electrodes 2165*a*-B may comprise, for example, metallic plates. In some embodiments, the source electrodes 2165*a*-B and the return electrodes 2166*a*-B on the dome head 2169 may be separated by an electrical insulator 2171. In some embodiments, a switch (not shown) may be located on the handle of the electrosurgical device 2110. The switch may selectively energize the internal source electrode 2170. In a deactivated state, the end effector 2126 may be used as a non-electrosurgical peanut dissector until cautery of tissue is desired. When cautery of a tissue section 2115 is desired, an operator may actuate the switch to active the internal source electrode 2170. The electrosurgical instrument 2110 may be used, for example, for spot cauterization and/or treatment of tissue sections in an active state.

For example, as shown in FIG. 31B, the exterior dome head 2169 may be coupled to the shaft 2114 by a flexible elastomer 2172. The flexible elastomer 2172 may allow the dome head 2169 to flex when a force is applied to the dome head 2169 by, for example, pushing the dome head 2169 into a tissue section. FIG. 31A illustrates the dome head 2169 in a flexed position, with an unflexed position being shown in phantom. FIGS. 31B and 31C each show a cross-section side-view of the end effector 2126. As shown in FIG. 31B, when the end effector 2126 is in an unflexed position, the internal source electrode 2170 is isolated from the dome head 2169. When a force is applied to the dome head 2169, for example, by tissue section 2115, the flexible elastomer 2172 allows the dome head 2169 to flex at the connection between the dome head 2169 and the shaft 2114. In a flexed position, as shown in FIG. 31C, the internal source electrode 2170 is in contact with at least one of the source electrodes 2165*a* of the dome head 2169.

FIG. 32 illustrates one embodiment of a multiple-electrode pencil tip end effector 2226 comprising flexible plate source electrodes 2265*a*-2265D. The source electrodes 2265*a*-D may comprise a flexible material configured to allow the source electrodes 2265*a*-D to flex relative to the return electrodes 2266*a*-2266D while maintaining a rigid dome head 2269. In other embodiments, the electrical insulator 2271 and/or the return electrodes 2266*a*-D may comprise a flexible material. When a force is applied to the dome head 2269, the flexible plate source electrodes 2265*a*-D may flex, causing at least one of the flexible plate source electrodes 2265*a*-D to contact the internal source electrode 2270. The internal source electrode 2270 may comprise a rigidly fixed electrode.

FIGS. 33A and 33B illustrate one embodiment of a multiple-electrode pencil tip end effector 2326. The multiple-electrode end effector 2326 may comprise one or more internal features to prevent contact between the internal source electrode 2370 and the return electrodes 2366*a*-D. The dome head 2369 may comprise a plurality of source electrodes 2365*a*-2365D. Each of the source electrodes 2365*a*-D may comprise an internal projection 2373*a*-2373D. The internal projections 2373*a*-D may be configured to allow a connection between the internal source electrode 2370 and at least one of the source electrodes 2365*a*-D while preventing contact between the internal source electrode 2370 and the plurality of return electrodes 2366*a*-2366D. In some embodiments, the internal projections 2373*a*-D may be configured to allow the internal source electrode 2370 to interact with only one of the plurality of source electrodes 2365*a*-D when force is applied to the dome head 2369.

In operation, a surgeon may apply a distal force to a handle (not shown) of a pencil-type electrosurgical instrument comprising a pencil-tip end effector, such as, for example, the multiple-electrode pencil tip end effector 2326 shown in FIGS. 33A and 33B. The distal force may push the dome head 2369 of the pencil tip end effector 2326 into contact with a tissue section 2315. The force applied by the tissue section 2315 to the dome head 2369 may cause the dome head 2369, one or more source electrodes 2365*a*-D, and/or the internal source electrode 2370 to flex, allowing a first source electrode 2365a nearest the tissue section 2315 to contact the internal source electrode 2370. When the internal source electrode 2370 contacts the first source electrode 2365a on the dome head 2369, current is allowed to flow through the tissue section 2315 and into the nearest return electrode in contact with the tissue section, such as the first return electrode 2366a. The current delivered through the first source electrode 2365a and the first return electrode 2366a to the tissue section 2315 may cause cautery of the tissue section 2315. In some embodiments, the current may flow along the shortest path, such as, for example, from the first source electrode 2365a, through a tissue section 2315, and back through the first return electrode 2366a. Cautery of the tissue may be limited to an area of tissue in contact with the pressurized surface of the dome head 2369. In some embodiments, the width of the electrical insulator 2371 located between the source electrode 2365a and the return electrode 2366a may determine the width of the cautery surface.

In some embodiments, a multiple-electrode pencil tip end effector, such as, for example, the pencil-tip end effectors 2126, 2226, 2326 illustrated in FIGS. 31A-33B, may comprise any suitable head-shape, such as, for example, a shovel head, a sharp pointed head, an asymmetric head, a cubic head, a cone head, and/or any other suitable shape. In some embodiments, the head may comprise a retractable blade such that, when desired, an operator may deploy the blade, activate the internal source electrode, and apply a pressure at the blade to simultaneously cut and cause cautery around the blade. In some embodiments, the pencil-tip end effectors 2226, 2326, 2426 may comprise interchangeable end effectors, such that an operator may vary tips during a surgical procedure without the need to change handles.

FIG. 34 illustrates one embodiment of a bipolar electrosurgical instrument 2410 comprising a bipolar pencil tip end effector 2426. The bipolar pencil-tip end effector 2426 may comprise a PTC electrode 2465. The PTC electrode 2465 may comprise a PTC material. The PTC electrode 2465 may comprise a central core electrode located at the distal end of the end effector 2426. A return electrode 2466 may be disposed on the distal end of the end effector 2426. The return electrode 2466 may comprise a ring electrode located concentrically with the PTC electrode 2465. An insulator 2471 may separate the PTC electrode 2465 and the return electrode 2466. Electrosurgical energy may be delivered to the PTC electrode 2465 and the return electrode 2466 from, for example, a generator such as the generator 120 illustrated in FIG. 1. In operation, the PTC electrode 2465 and the return electrode 2466 may be configured to deliver bipolar electrosurgical energy to a tissue section in contact with the end effector 2426. As the temperature of the tissue section increases, the PTC material of the PTC electrode 2465 may limit the current flow through the tissue section, providing temperature control during tissue ablation. In the embodiment of FIG. 34, the return electrode 2466 fully surrounds the PTC electrode 2465, which may minimize stray currents during tissue ablation. The end effector 2426 may be suitable for various tissue treatments, including, for example, spinal disc ablation, endometrial ablation, and/or other precision ablation procedures.

FIG. 35 illustrates one embodiment of an end effector 2526 comprising a PTC electrode 2565 and a return electrode 2566. The PTC electrode 2565 and the return electrode 2566 may comprise hemispheres on the tip of the end effector 2526. The PTC electrode 2565 and the return electrode 2566 hemispheres may be separated by an insulator 2571. In some embodiments, such as the embodiment shown in FIG. 36A, the space between the PTC electrode 2665 and the return electrode 2666 hemispheres may define a step/cavity for receiving tissue therebetween. FIG. 36B illustrates treatment of a tissue section 2615 utilizing the end effector 2626. An operator may apply a distal force to a handle (not shown) coupled to the end effector 2626. The distal force may cause the end effector 2626 to apply a force to the tissue section 2615. An electrosurgical signal may be applied to the tissue section 2615 by the PTC electrode 2665 and the return electrode 2666. The combination of the distal force and the electrosurgical energy may be used for spot cautery and/or the generation of an otomy within a patient.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. An end effector for an electrosurgical device, the end effector comprising:
    a first electrode; and
    a second electrode movable from a first position to a second position when a force is applied to the end effector, wherein the first electrode and the second electrode define a treatment area when the second electrode is in the second position.

2. The end effector of clause 1, wherein the end effector comprises a third electrode movable from a first position and a second position, wherein the second electrode and the third electrode are disposed on opposite sides of the first electrode, wherein the second electrode and the third electrode have an opposite polarity of the first electrode, and wherein when a force is applied to the end effector the second electrode and the third electrode transition from the first position to the second position to define the treatment area therebetween.

3. The end effector of clause 2, wherein the first electrode, the second electrode, and the third electrode are slidably deployable from the shaft, wherein the second electrode and the third electrode are biased away from the first electrode, and wherein the first electrode, the second electrode, and the third electrode may be energized when in a deployed state.

4. The end effector of clause 2, comprising a deformable tip, wherein when a force is applied to the first electrode, the deformable tip deforms to move the second electrode and the third electrode into the second position to define a treatment area therebetween, and wherein the first electrode comprises a high pressure electrode.

5. The end effector of clause 4, wherein the high pressure electrode comprises a blade.

6. The end effector of clause 4, wherein the deformable tip comprises a deformable tube.

7. The end effector of clause 6, wherein the deformable tip comprises a circular orientation in a rest position, and wherein the deformable tip assumes an oval cylinder configuration when the force is applied to the tip.

8. The end effector of clause 2, comprising:
    a plurality of source electrodes and a plurality of return electrodes, wherein the plurality of source electrodes and the plurality of return electrodes are arranged in an alternating configuration, wherein the plurality of source electrodes and the plurality of return electrodes define a cavity, and wherein the plurality of source electrodes and the plurality of return electrodes are separated by an insulator; and
    an internal source electrode disposed within the cavity, wherein the source electrode is configured to make contact with at least one of the plurality of source electrodes when a force is applied to the electrosurgical tip.

9. The end effector of clause 8, comprising at least one internal connection point on each of the plurality of source electrodes, wherein the internal connection point is configured to allow a connection between the plurality of source electrodes and the internal source electrode, and wherein the internal connection point is configured to prevent a connection between the plurality of return electrodes and the internal source electrode.

10. The end effector of clause 9, comprising a flexible connection at a proximal end of the end effector, wherein when a force is applied to the end effector, the flexible connection flexes to deflect at least one of the plurality of source electrodes into contact with the internal source electrode.

11. The end effector of clause 9, comprising a flexible connection at a proximal end of the internal source electrode, wherein when a force is applied to the end effector, the flexible connection flexes to deflect the internal source electrode into contact with at least one of the source electrodes.

12. The end effector of clause 1, wherein the first electrode comprises a positive temperature coefficient (PTC) material configured to limit the current flow through the first electrode based on the temperature of the first electrode.

13. The end effector of clause 12, wherein the first electrode is disposed on a distal end of the end effector, and wherein the second electrode comprises a ring located concentric with the first electrode.

14. The end effector of clause 1, comprising an electrosurgical generator coupled to the end effector, wherein the electrosurgical generator is configured to produce a high frequency, multi-phase electrosurgical signal, wherein the electrosurgical generator is coupled to the first electrode and the second electrode.

15. A base cap configured to interface with an electrosurgical device, the base cap comprising:
    an electrode layer configured to provide electrosurgical signals to a tissue section in contact with the base cap;
    a heat sink layer configured to prevent heat transfer between the base cap and the electrosurgical device; and a sealing layer configured to seal the base cap, wherein the base cap is removably coupled to the electrosurgical device.

16. The base cap of clause 15, wherein the base cap is configured to removably couple to a lower jaw of the electrosurgical device.

17. The base cap of clause 16, comprising at least one molded hook configured to interface with at least one overhang formed on the lower jaw of the electrosurgical device.

18. The snap cap of clause 15, wherein the electrode layer comprises a direct contact metal electrode.

19. The snap cap of clause 15, wherein the electrode comprises an inductive coupling electrode.

20. The snap cap of clause 15, comprising a flex circuit deposited on the sealing layer, wherein the flex circuit is configured to provide a connection between the electrode layer and a source and return path within the electrosurgical device.

21. An electrosurgical device comprising:
a waveform generator configured to produce an electrosurgical signal comprising at least a first phase and a second phase;
a first conductor configured to receive the first phase of the electrosurgical signal; and
a second conductor configured to receive the second phase of the electrosurgical signal.

22. The electrosurgical device of clause 21, comprising a third conductor, wherein the electrosurgical signal comprises a third phase, and wherein the third conductor is configured to receive the third phase of the electrosurgical signal.

23. The electrosurgical device of clause 22, comprising a laminate strip coupled to a distal end of the electrosurgical device, the laminate strip comprising at least the first flat conductor flex circuit, the second flat conductor flex circuit, and the third flat conductor flex circuit.

24. The electrosurgical device of clause 22, the waveform generator comprising:
a first signal generator to generate the first phase of the electrosurgical signal;
a second signal generator to generate the second phase of the electrosurgical signal; and
a third signal generator to generate the third phase of the electrosurgical signal.

25. The electrosurgical (RF) device of clause 22, wherein the first conductor, the second conductor, and the third conductor comprise a flat, flexible circuit.

26. The electrosurgical device of clause 25, wherein the flat, flexible circuit comprises a circuit path of approximately 0.1"×0.01".

27. An end effector for an electrosurgical device, the end effector comprising:
a first jaw member comprising a first electrode; and
a second jaw member comprising a second electrode, wherein the first and second electrodes comprise a fluoropolymer material comprising an electrically conductive mica additive.

28. The end effector of clause 27, wherein the fluoropolymer comprises polytetrafluoroethylene (PTFE).

29. The end effector of clause 27, wherein the fluoropolymer material comprises a thickness of 5-21 microns, and wherein the fluoropolymer material comprise 0.1-10% of the electrically conductive mica additive by weight.

30. An end effector for an electrosurgical device, the end effector comprising:

a source electrode comprising a positive temperature controlled (PTC) material; and
a return electrode electrically isolated from the source electrode, wherein the source electrode and the return electrode are configured to receive a bipolar electrosurgical signal.

31. The end effector of clause 30, wherein the end effector comprises a spherical tip, wherein the source electrode comprises a central core of the spherical tip, and wherein the return electrode comprises a ring electrode disposed on the spherical tip and concentric with the source electrode.

32. The end effector of clause 30, wherein the end effector comprises:
a first hemisphere comprising the source electrode;
a second hemisphere comprising the return electrode; and
an insulator located between the source electrode and the return electrode.

33. The end effector of clause 32, wherein the insulator comprises an air gap.

34. An electrosurgical instrument comprising:
a handle;
a shaft extending distally from the handle;
an end effector coupled to a distal end of the handle, the end effector comprising:
an upper jaw comprising a first electrode;
a lower jaw comprising a second electrode;
a power tip extending from a distal end of the lower jaw, wherein the power tip comprises an electrode configured to receive electrosurgical energy.

35. The electrosurgical instrument of clause 34, wherein the electrosurgical instrument is coupled to a generator, wherein the generator comprises a bipolar signal generator and a harmonic signal generator, wherein the bipolar signal generator is configured to generate bipolar electrosurgical signal, wherein the harmonic signal generator is configured to generate a sub-100 kHz signal, wherein the first and second electrodes are coupled to the bipolar signal generator, and wherein the power tip is coupled to the harmonic signal generator.

36. The electrosurgical instrument of clause 34, comprising a switch configured to control operation of the first electrode, the second electrode, and the power tip, wherein when the switch is in a first position, the first electrode and the second electrode are configured to receive a bipolar electrosurgical signal, and wherein when the switch is in a second position, the power tip is configured to receive a monopolar electrosurgical signal.

37. A monopolar add-on for an electrosurgical device comprising a power tip, the monopolar add-on comprising:
a handle configured to interface with a shaft of the electrosurgical device;
a slip ring coupled to the handle, the slip ring configured to interface with a conductor disposed within the shaft of the electrosurgical device, wherein the conductor is coupled to a power tip located at the distal end of the electrosurgical instrument;
a cable coupled to the slip ring, the cable configured to couple to a monopolar generator; and
a switch configured to control delivery of a monopolar electrosurgical signal from the monopolar generator to the power tip.

What is claimed is:
1. An electrosurgical device, comprising:
an end effector comprising:
a first electrode;

a second electrode movable from a first position to a second position when a force is applied to the end effector; and a channel within which a moveable member is configured to slide to open and close an upper jaw and a lower jaw, wherein the first electrode and the second electrode define a treatment area when the second electrode is in the second position; and a base cap configured to interface with the end effector, the base cap comprising:

an electrode layer configured to provide electrosurgical signals to a tissue section in contact with the base cap, the electrode layer comprising a direct contact metal electrode configured for direct application of electrosurgical energy to the tissue section;

a heat sink layer configured to prevent heat transfer between the base cap and the end effector;

a sealing layer configured to seal the base cap;

at least one molded hook configured to interface with at least one overhang formed on the lower jaw of the end effector; and a flex circuit deposited on the sealing layer, wherein the electrode layer is connected to a source and return path through the flex circuit, wherein the heat sink layer is arranged between the electrode layer and the end effector when the base cap interfaces with the end effector, wherein the base cap is configured to cover an entire portion of the channel to protect the channel from debris and fouling during the direct application of electrosurgical energy to the tissue section.

2. The electrosurgical device of claim 1, wherein the end effector comprises a third electrode movable from the first position to the second position, wherein the second electrode and the third electrode are disposed on opposite sides of the first electrode, wherein the second electrode and the third electrode have an opposite polarity of the first electrode, and wherein, when a force is applied to the end effector, the second electrode and the third electrode transition from the first position to the second position to define the treatment area therebetween.

3. The electrosurgical device of claim 1, wherein the first electrode comprises a positive temperature coefficient (PTC) material configured to limit a current flow through the first electrode based on a temperature of the first electrode.

4. The electrosurgical device of claim 3, wherein the first electrode is disposed on a distal end of the end effector, and wherein the second electrode comprises a ring located concentric with the first electrode.

5. The electrosurgical device of claim 1, further comprising:

an electrosurgical generator coupled to the end effector, wherein the electrosurgical generator is configured to produce a high frequency, multi-phase electrosurgical signal, and wherein the electrosurgical generator is coupled to the first electrode and the second electrode.

* * * * *